United States Patent [19]
Shimotani et al.

[11] Patent Number: 5,573,006
[45] Date of Patent: Nov. 12, 1996

[54] BODILY STATE DETECTION APPARATUS

[75] Inventors: Mitsuo Shimotani; Minoru Nishida; Akira Okada; Toshihide Satake; Shoichi Washino; Futoshi Okawa; Hiromi Terashita, all of Hyogo, Japan

[73] Assignee: Mitsubishi Denki Kabushiki Kaisha, Tokyo, Japan

[21] Appl. No.: 330,322

[22] Filed: Oct. 27, 1994

[30] Foreign Application Priority Data

Mar. 10, 1994 [JP] Japan ................................. 6-039887

[51] Int. Cl.$^6$ ...................................................... A61B 13/00
[52] U.S. Cl. ............................................ 128/745; 340/575
[58] Field of Search ............................ 128/745; 340/573, 340/575, 576

[56] References Cited

U.S. PATENT DOCUMENTS

| | | | |
|---|---|---|---|
| 4,594,583 | 6/1986 | Seko et al. | 340/576 |
| 4,967,186 | 10/1990 | Ludmirsky et al. | 340/575 |
| 5,311,879 | 5/1994 | Yamada et al. | 128/745 |
| 5,402,109 | 3/1995 | Mannik | 340/575 |

OTHER PUBLICATIONS

A. Tomono, et al "A TV Camera System Which Extracts Feature Point For Non–Contact Eye Movement Detection" SPIE vol. 1194 Optics, Illumination and Image Sensing for Machine Vision IV (1989).

Primary Examiner—Max Hindenburg
Attorney, Agent, or Firm—Wolf, Greenfield & Sacks, P.C.

[57] ABSTRACT

A bodily state detection apparatus comprising a CCD camera, an infrared LED device, a pickup image memory, a pupil extraction circuit and a bodily state judgment circuit. The CCD camera inputs images of a predetermined area including the subject person's face. The infrared LED device illuminates the subject person in such a way that the optical axis of the camera and the direction of the illumination coincide with each other. The pickup image memory stores temporarily the output data of the CCD camera. The pupil extraction circuit extracts the subject person's pupil position from the pickup images. The bodily state judgment circuit judges the subject person's bodily state by use of the result of pupil extraction performed by the pupil extraction circuit.

15 Claims, 32 Drawing Sheets

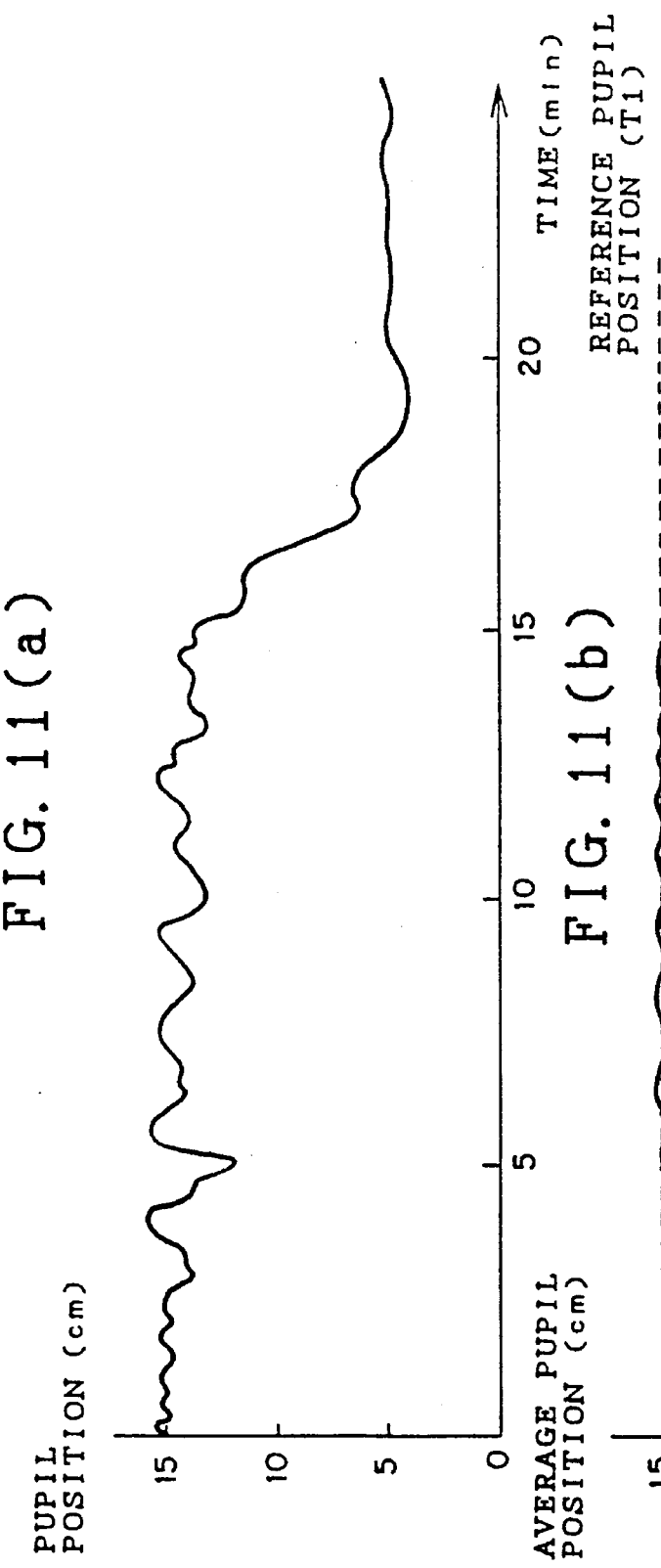
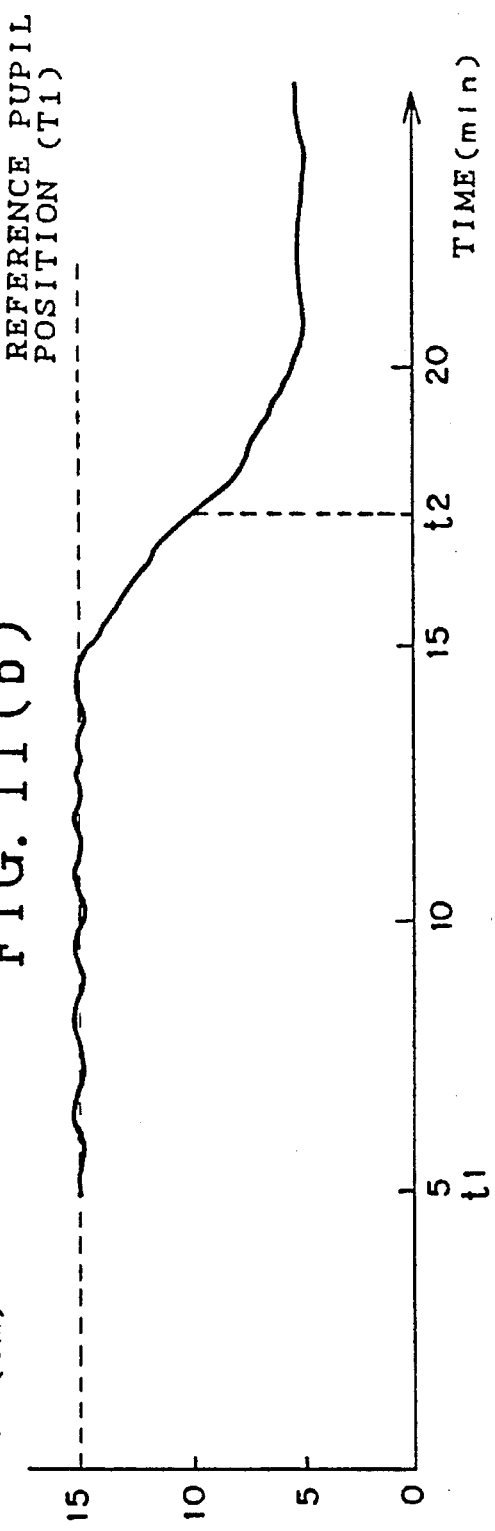
FIG. 11(a)
FIG. 11(b)

FIG. 14(a)
EYE IMAGE    EXTRACTED PUPIL SHAPE
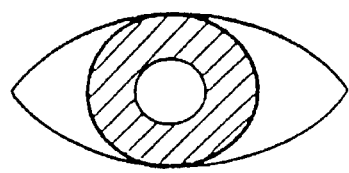 ⇒ 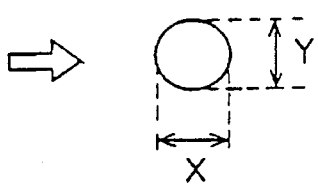
FIG. 14(b)
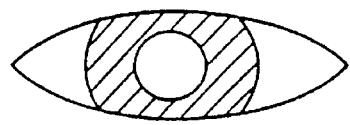 ⇒ 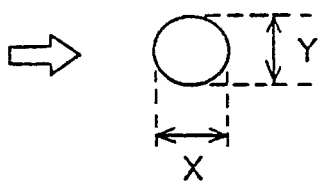
FIG. 14(c)
 ⇒ 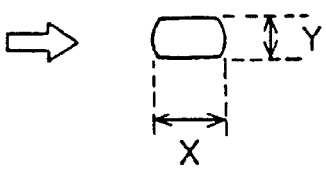

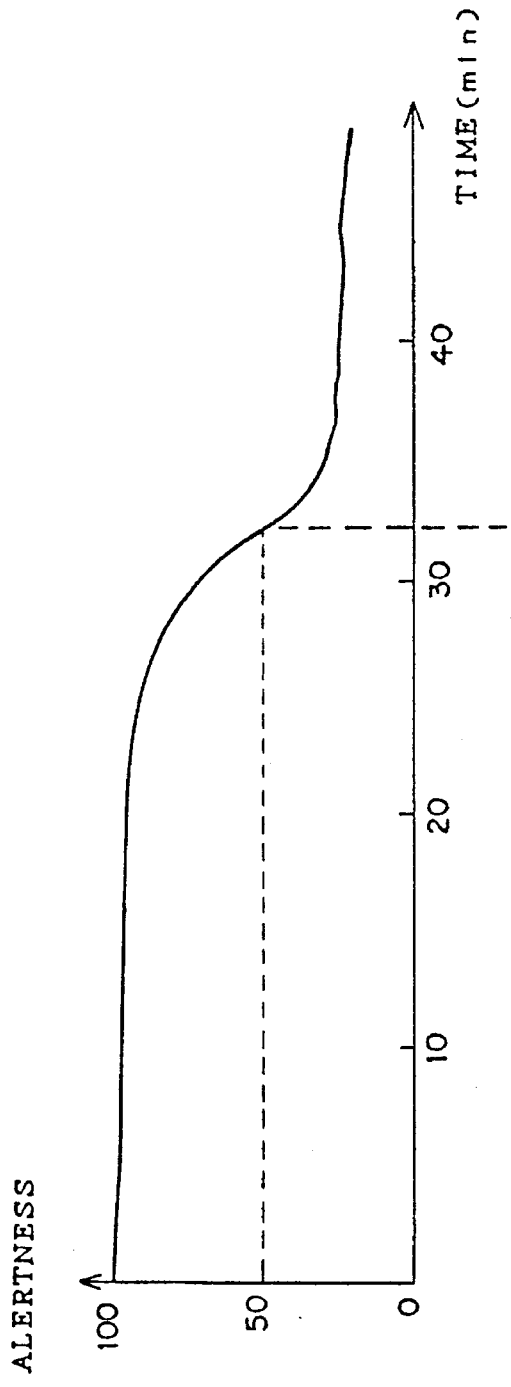
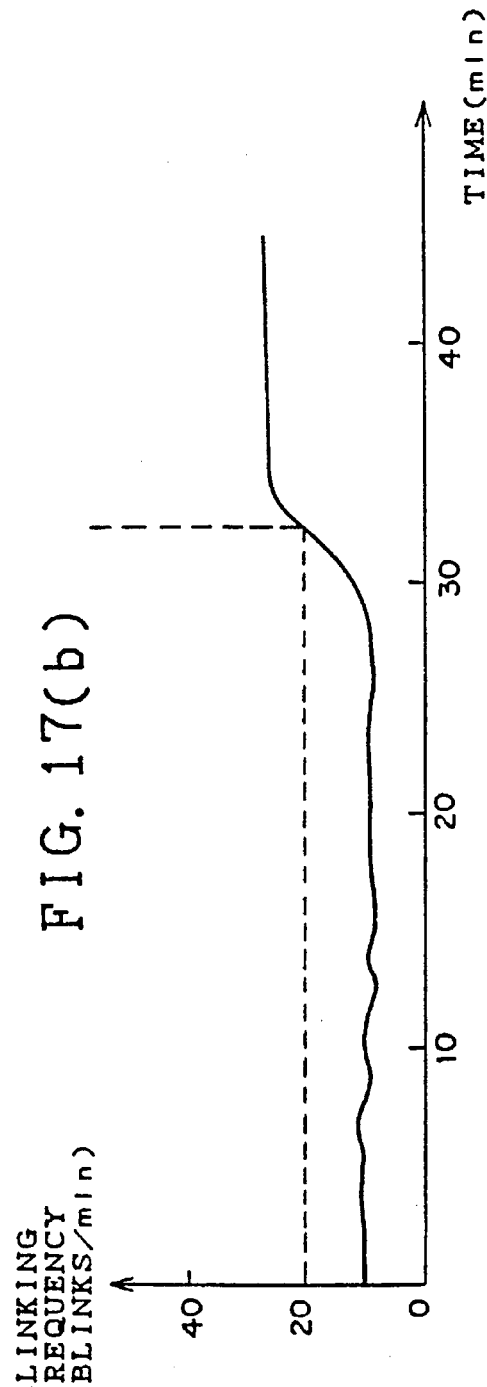

FIG. 31(a)
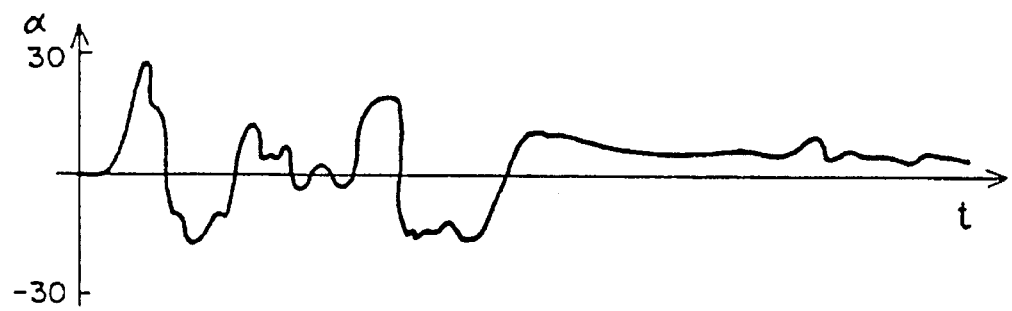
FIG. 31(b-1)
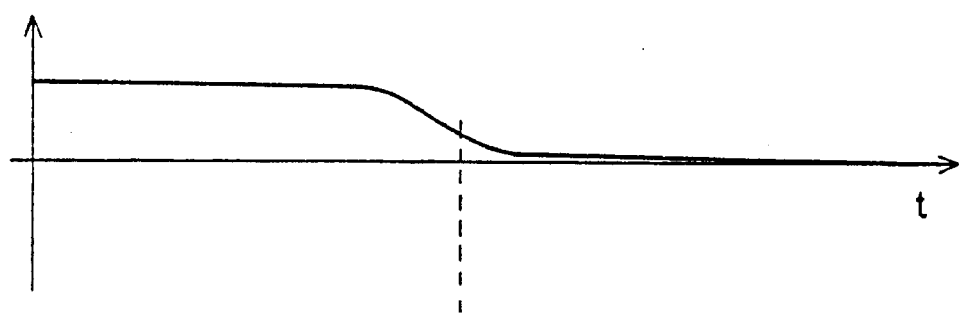
FIG. 31(b-2)
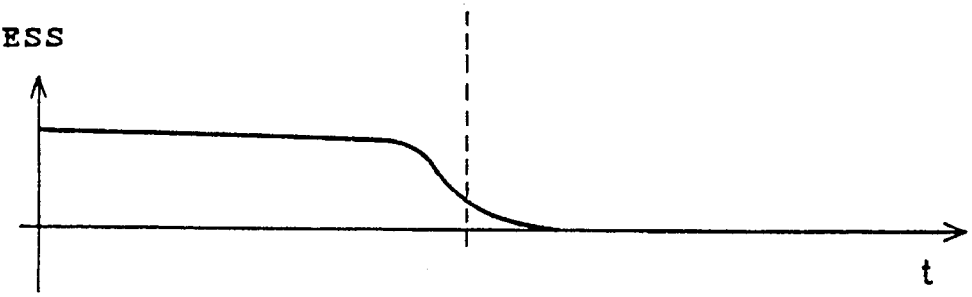

DISTANCE: SHORT

DISTANCE: LONG

BODILY STATE DETECTION APPARATUS

BACKGROUND OF THE INVENTION

1. Field of the Invention

The present invention relates to a bodily state detection apparatus that detects the bodily state of the subject person by taking pictures of the retinal reflection obtained with the so-called coaxial illumination directed to that person. More particularly, the invention relates to a physiological or psychological state detection apparatus that detects primarily the alertness or the tenseness of the subject person based on the pictures taken of that person, practiced illustratively as an apparatus that detects the drowsiness or the psychological state of a vehicle driver.

2. Description of the Related Art

Conventional apparatuses offering the above-stated features include the organic state detection apparatus disclosed in Japanese Patent Laid-open Application No. Sho 63-217500 and the driver drowsiness prevention apparatus disclosed in Japanese Patent Publication No. Hei 3-14655. These apparatuses each have transceiver means mounted on the eyeglass frame worn by the subject person. In operation, the apparatus senses the reflection from the eyelids or from the corneas to see if the eyelids are open or closed, thereby detecting the bodily state of the subject person. A major disadvantage of this type of apparatuses is the annoying need for the subject person to wear the eyeglass frame.

There exist other conventional apparatuses capable of detecting the bodily state on a noncontact basis without requiring the subject person to wear any detectors that would hamper the proper work or operation performed by that person. One such apparatus is the eye position recognition apparatus disclosed in Japanese Patent Laid-open Application No. Sho 60-158303. The disclosed apparatus comprises a camera that takes face pictures of the subject person, and means for detecting pupil and eyelid movements through the image processing based on the pictures taken. FIG. 1 is a schematic view of the disclosed apparatus used as a drowsiness detection apparatus. In FIG. 1, reference numeral 1 is a subject person; 2 is an infrared LED which illuminates the subject person 1 and which has a center illumination wavelength of 860 nm; 3 is a CCD camera that converts face pictures of the subject person 1 into electrical signals; 10 is a pickup image memory that stores temporarily the output data of the CCD camera 3; 20 is a feature point extraction circuit that extracts the pupil movement from the data in the pickup image memory 10; and 40 is a drowsiness judgement circuit that checks to see if the subject person is drowsy by detecting the eyelid movement from the data furnished by the feature point extraction circuit 20.

In operation, the infrared LED 2 illuminates the subject person 1. The image of the subject person 1 is input to the CCD camera 3 so positioned as to take pictures of a predetermined area including the face of the subject person 1. The pickup input image memory 10 receives and accommodates the output data from the CCD camera 3. The feature point extraction circuit 20 extracts the pupil position, eye position, face orientation and other features through image processing based on the data from the pickup input image memory 10. When, say, the pupil movement is extracted by the feature point extraction circuit 20, the drowsiness judgement circuit 40 detects the apparent presence or absence of the pupils. If the pupils are apparently absent for a predetermined period of time, the drowsiness judgement circuit 40 determines that the subject person 1 is being drowsy.

FIG. 2 is a view of an infrared image used by the conventional apparatus of FIG. 1. In FIG. 2, reference numeral 4 is the iris, 5 is the sclera, 6 is the pupil, and 7 is the face surface. In the image thus obtained, the face surface 7 appears a little dark, the sclera 5 darker than the face surface 7, the iris 4 darker than the sclera 5, and the pupil 6 still darker than the iris 4.

One disadvantage of the bodily state detection apparatus structured as outlined above is that it needs complicated image processing whereby the eyelid movement is to be detected. Specifically, the obtained image is subjected to filter computation and then to edge detection. The shape of the detected edge is used to perform a pattern recognition process by which to find the circular arcs representing the eyelids. With the eyelid position determined, the eyelid shape is calculated in further detail. During edge detection, the circular arcs are hard to find if the edge is not detected smoothly due to the presence of noise or other disturbances. All this contributes to making the image processing a time-consuming and complicated procedure.

Meanwhile, there has been proposed a system that detects the eye position through very simple image processing such as binary processing. That system comprises a coaxial illumination device that illuminates the face surface of the subject person to let pictures of the retinal reflection be taken for the simplified image processing, as discussed in "Prototype of Gaze Direction Detection Apparatus Permitting Pupil Data Extraction and Head Movement" (Technical Report of the Institute of Electronics, Information and Communication Engineers of Japan; D-II, Vol. J76-D-II, No. 3). The coaxial illumination device is a device wherein the optical axis of the camera and the direction of illumination coincide with each other.

SUMMARY OF THE INVENTION

It is therefore an object of the present invention to provide a bodily state detection apparatus that extracts the iris image of the subject person through simple image processing, thereby detecting the bodily state of that person with ease on a noncontact basis.

It is another object of the invention to provide a bodily state detection apparatus that obtains facial feature quantities more directly, thereby enhancing the accuracy of bodily state detection.

It is a further object of the invention to provide a bodily state detection apparatus that utilizes time series averaged data to improve the accuracy of bodily state detection.

It is an even further object of the invention to provide a bodily state detection apparatus that determines the degree of alertness of the subject person by detecting blinking movements of that person's eyes.

It is a still further object of the invention to provide a bodily state detection apparatus that determines the degree of alertness or tenseness of the subject person by detecting blinking movements of that person's eyes.

It is a yet further object of the invention to provide a bodily state detection apparatus that detects the physiological state or the degree of tenseness of the subject person.

It is another object of the invention to provide a bodily state detection apparatus that ensures high reliability in bodily state detection by evaluating the pupil size correctly regardless of the changing face orientation of the subject person.

It is a further object of the invention to provide a bodily state detection apparatus that determines the degree of alertness of the subject person more reliably than ever by unfailingly detecting blinking movements of that person's eyes.

It is an even further object of the invention to provide a bodily state detection apparatus that determines the degree of tenseness of the subject person.

It is a still further object of the invention to provide a bodily state detection apparatus that ensures high degrees of accuracy in detecting the bodily state of the subject person.

In achieving the foregoing and other objects of the present invention and according to a first aspect thereof, there is provided a bodily state detection apparatus comprising: optical input means for receiving images of a predetermined area including the face of a subject person; illumination means for illuminating the subject person in such a manner that the direction of the illumination coincides substantially with the optical axis connecting the subject person with the optical input means; pupil extraction means for extracting either the pupil position or the pupil shape of the subject person from the images thereof output from the optical input means; and bodily state judgment means for judging the bodily state of the subject person by use of the result of the pupil extraction performed by the pupil extraction means.

As outlined, the bodily state detection apparatus according to the first aspect of the invention allows either the pupil position or the pupil shape of the subject person to be detected using the setup wherein the direction of the illumination coincides substantially with the optical axis connecting the subject person with the optical input means. The apparatus thus extracts the subject person's pupils through simplified image processing for easy, noncontact judgment of that person's bodily state.

According to a second aspect of the invention, there is provided a bodily state detection apparatus comprising: optical input means for receiving images of a predetermined area including the face of a subject person; illumination means for illuminating the subject person in such a manner that the direction of the illumination coincides substantially with the optical axis connecting the subject person with the optical input means; pupil extraction means for extracting either the pupil position or the pupil shape of the subject person from the images thereof output from the optical input means; search range definition means for defining the range of search for feature points in the subject person's face on the basis of the result of the pupil extraction performed by the pupil extraction means; feature quantity extraction means for extracting either the position or the shape of the feature points in the range defined by the search range definition means; and bodily state judgment means for judging the bodily state of the subject person by use of the result of the feature quantity extraction performed by the feature quantity extraction means or by use of the result of pupil extraction performed by the pupil extraction means.

As outlined, the bodily state detection apparatus according to the second aspect of the invention defines the range of search for feature points in the subject person's face on the basis of the result of the pupil extraction. The apparatus then extracts either the position or the shape of the feature points in the range so defined, and judges the subject person's bodily state on the basis of the result of the pupil extraction or the result of the feature quantity extraction. By acquiring feature quantities more directly than before, the apparatus enhances the accuracy of bodily state detection.

In a preferred structure according to a third aspect of the invention, the bodily state detection apparatus further comprises extraction result storage means for storing the result of the pupil extraction or feature quantity extraction, wherein the bodily state judgment means judges the bodily state of the subject person in accordance with the stored contents of the extraction result storage means.

With this structure, the extraction result storage means of the apparatus stores the result of the pupil extraction or feature quantity extraction in such a manner that the stored contents of that means are used to judge the subject person's bodily state. The structure allows the apparatus to utilize time series averaged data, thereby enhancing the accuracy of bodily state detection.

In a preferred structure according to the fourth aspect of the invention, the bodily state detection apparatus further comprises eyelid opening estimation means for estimating the degree of eyelid opening of the subject person in accordance with the pupil shape extracted by the pupil extraction means, wherein the bodily state judgment means judges the bodily state of the subject person on the basis of the estimated degree of eyelid opening.

With this structure, the eyelid opening estimation means of the apparatus estimates the degree of eyelid opening of the subject person in accordance with the pupil shape extracted by the pupil extraction means, the estimated degree of eyelid opening being used to judge the subject person's bodily state. From the bodily state so judged, the apparatus recognizes the subject person's blinking state and the degree of his alertness accordingly.

In a preferred structure according to a fifth aspect of the invention, the bodily state detection apparatus further comprises blinking frequency estimation means for estimating the frequency of blinking of the subject person in accordance with the result of the pupil extraction, wherein the bodily state judgment means judges the bodily state of the subject person on the basis of the estimated frequency of blinking.

With this structure, the blinking frequency estimation means estimates the subject person's blinking frequency from the result of the pupil extraction. The estimated blinking frequency is used by the bodily state judgment means to judge the subject person's bodily state. With the subject person's blinking frequency estimated as in the preceding structure, it is possible for the apparatus to recognize the degree of alertness or tenseness of that person.

In a preferred structure according to a sixth aspect of the invention, the bodily state detection apparatus further comprises pupil waveform output means for measuring the diameter of the pupils from the pupil shape extracted by the pupil extraction means and for outputting waveforms of expansion and contraction of the pupils of the subject person, wherein the bodily state judgment means judges the subject person's bodily state in accordance with the waveforms of expansion and extraction of that person's pupils.

With this structure, the pupil waveform output means measures the diameter of the pupils from the pupil shape extracted by the pupil extraction means and outputs waveforms of expansion and contraction of the subject person's pupils. After determining how the subject person's pupils expand and contract, the apparatus judges the physiological state or the degree of alertness of that person.

In a preferred structure according to a seventh aspect of the invention, the pupil waveform output means measures the maximum diameter of the pupils from the pupil shape extracted by the pupil extraction means, whereby the waveforms of expansion and contraction of the subject person's pupils are output.

With this structure, the ability to measure the maximum diameter of the pupils from the extracted pupil shape makes it possible to estimate correctly the pupil size regardless of the changing face orientation. The apparatus thus provides higher reliability than before.

In a preferred structure according to an eighth aspect of the invention, the bodily state detection apparatus further comprises eyelid opening calculation means for calculating the degree of eyelid opening of the subject person in accordance with the result of eyelid feature quantity extraction performed by the feature quantity extraction means, wherein the bodily state judgment means judges the bodily state of the subject person on the basis of the calculated degree of eyelid opening.

With this structure, the feature quantity extraction means extracts the eyelids as feature quantities. From the result of the extraction, the eyelid opening calculation means calculates the degree of eyelid opening. Based on the calculated degree of eyelid opening, the bodily state judgment means judges the subject person's bodily state. Because the subject person's blinking state is known unfailingly in the above manner, it is possible for the apparatus to judge that person's degree of alertness more reliably than before.

In a preferred structure according to a ninth aspect of the invention, the bodily state detection apparatus further comprises gaze direction detection means for detecting the gaze direction of the subject person in accordance with the result of pupil extraction by the pupil extraction means and with the result of feature quantity extraction by the feature quantity extraction means, wherein the bodily state judgment means judges the bodily state of the subject person on the basis of time series patterns of the subject person's gaze direction.

With this structure, the gaze direction detection means detects the subject person's gaze direction from the result of pupil extraction as well as from the result of feature quantity extraction. When the bodily state judgment means judges the subject person's bodily state based on the time series patterns of the subject person's gaze direction, the apparatus finds the degree of tenseness of that person.

In a preferred structure according to a tenth aspect of the invention, the bodily state detection apparatus further comprises stimulus generation means for generating stimulus to the subject person depending on the primary result of judgment by the bodily state judgment means, wherein the bodily state judgment means makes a secondary judgment on the bodily state of the subject person in accordance with the status of either the pupils or the feature points before and after the generation of the stimulus.

With this structure, the stimulus generation means generates stimulus to the subject person depending on the primary result of judgment by the bodily state judgment means. A secondary judgment on the subject person's bodily state is made based on the status of either the pupils or the feature points before and after the generation of the stimulus. Where changes are determined in the pupil or feature point status between before and after the generation of the stimulus, the apparatus affords higher accuracy in bodily state detection.

In a preferred structure according to an eleventh aspect of the invention, the bodily state detection apparatus further comprises face distance measurement means for measuring the distance between a predetermined position and the face of the subject person, wherein the pupil extraction means or the feature quantity extraction means corrects the extracted pupil shape or feature quantities in accordance with the measured distance.

With this structure, the face distance measurement means measures the distance between the predetermined position and the subject person's face. With the face distance so measured, the apparatus corrects the pupil shape or the feature quantities correspondingly, thus enhancing the accuracy of bodily state detection.

In a preferred structure according to a twelfth aspect of the invention, the bodily state detection apparatus further comprises illumination measurement means for measuring the intensity of illumination near the subject person, wherein the bodily state judgment means judges the bodily state of the subject person in accordance with the result of the measured intensity of illumination.

With this structure, the intensity of illumination is measured near the subject person. Based on the illumination intensity so measured, the apparatus judges the subject person's bodily state with higher accuracy than before.

In a preferred structure according to a thirteenth aspect of the invention, the bodily state detection apparatus further comprises face orientation estimation means for measuring the face orientation of the subject person, wherein the pupil extraction means or feature quantity extraction means corrects the pupil shape or feature quantities in accordance with the measured face orientation.

With this structure, the face orientation estimation means measures the subject person's face orientation. With the face orientation so determined, the apparatus corrects the pupil shape or feature quantities correspondingly, whereby the accuracy of bodily state detection is boosted.

In a preferred structure according to a fourteenth aspect of the invention, the bodily state detection apparatus further comprises magnification means for magnifying the images of the predetermined area including the face of the subject person, the magnified images being input to the optical input means.

With this structure, the magnification means magnifies the images of the predetermined area including the subject person's face. When the magnified images are input to the optical input means, the apparatus detects the subject person's bodily state with higher accuracy than before.

Other objects, features and advantages of the present invention will become apparent in the following specification and accompanying drawings.

BRIEF DESCRIPTION OF THE DRAWINGS

FIGS. 11(a) and 11(b) are graphic representations showing how the second embodiment illustratively works;

FIGS. 14(a), 14(b), and 14(c) are a set of views depicting how the fourth embodiment works illustratively;

FIGS. 17(a) and 17(b) are another graphic representation depicting how the fifth embodiment works illustratively;

FIGS. 31(a), 31(b-1) and 31(b-2) are graphic representations showing how the tenth embodiment works illustratively;

DETAILED DESCRIPTION OF THE PREFERRED EMBODIMENTS

The preferred embodiments of the invention will now be described in detail with reference to the accompanying drawings.

First Embodiment

Figure 1:
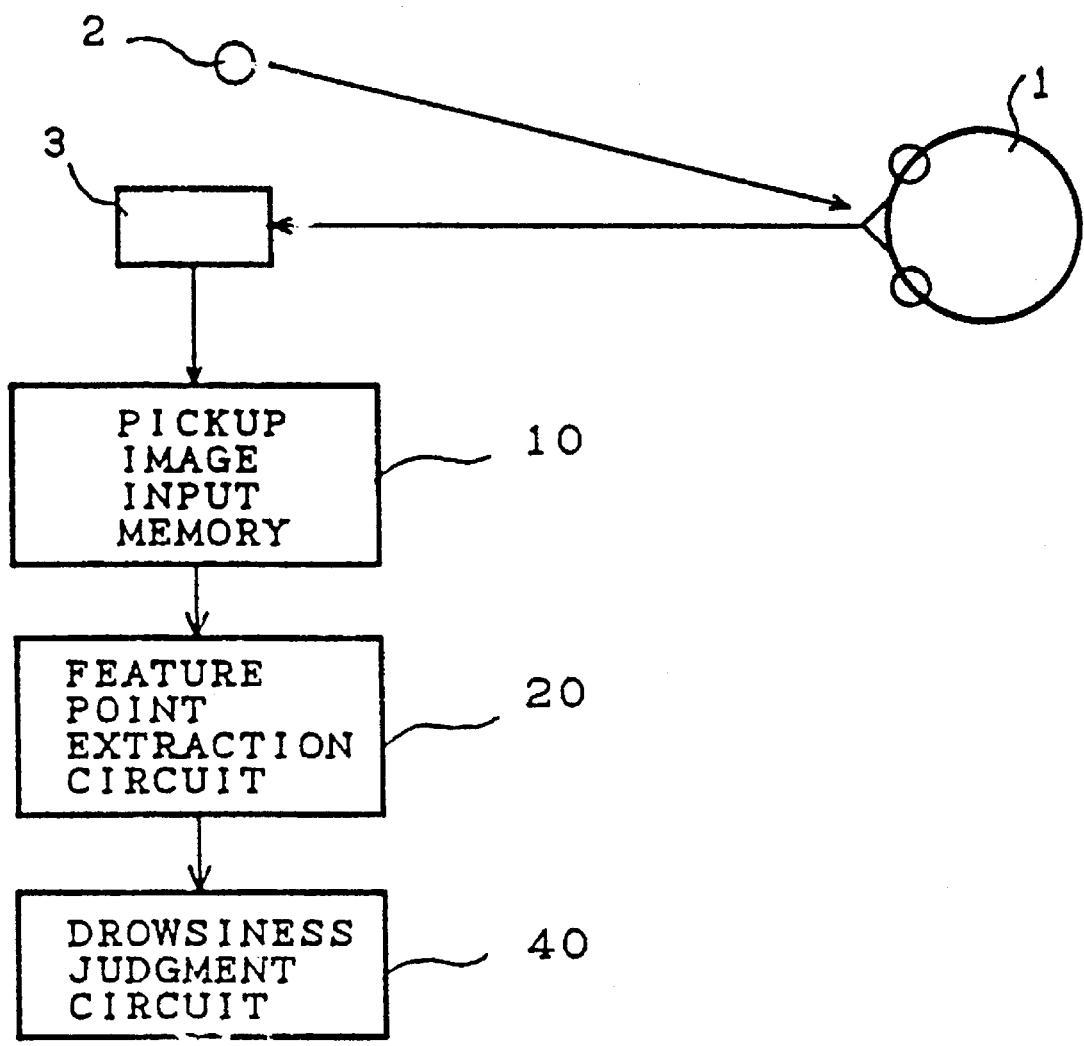
FIG. 1 is a schematic view of a conventional bodily state detection apparatus.
Figure 2:
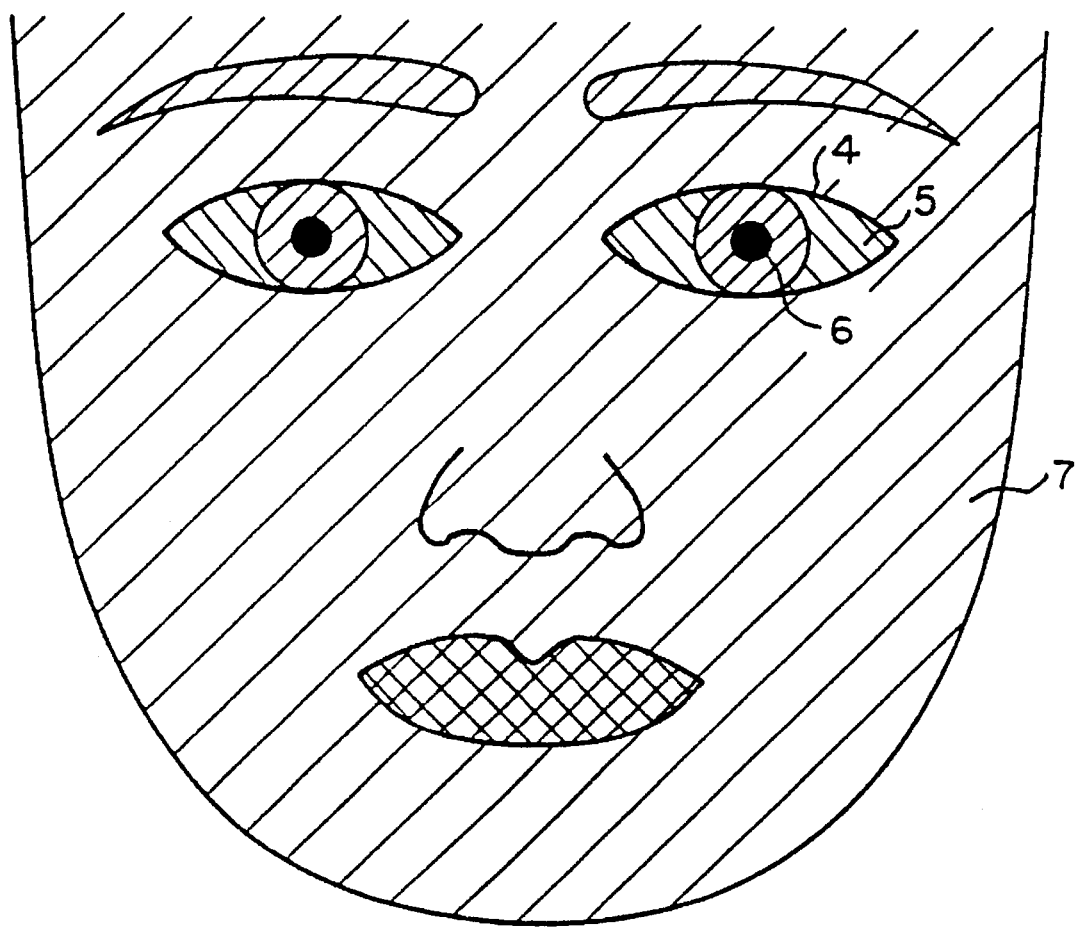
FIG. 2 is a view of a pickup image taken by optical input means of the conventional bodily state detection apparatus.
Figure 3:
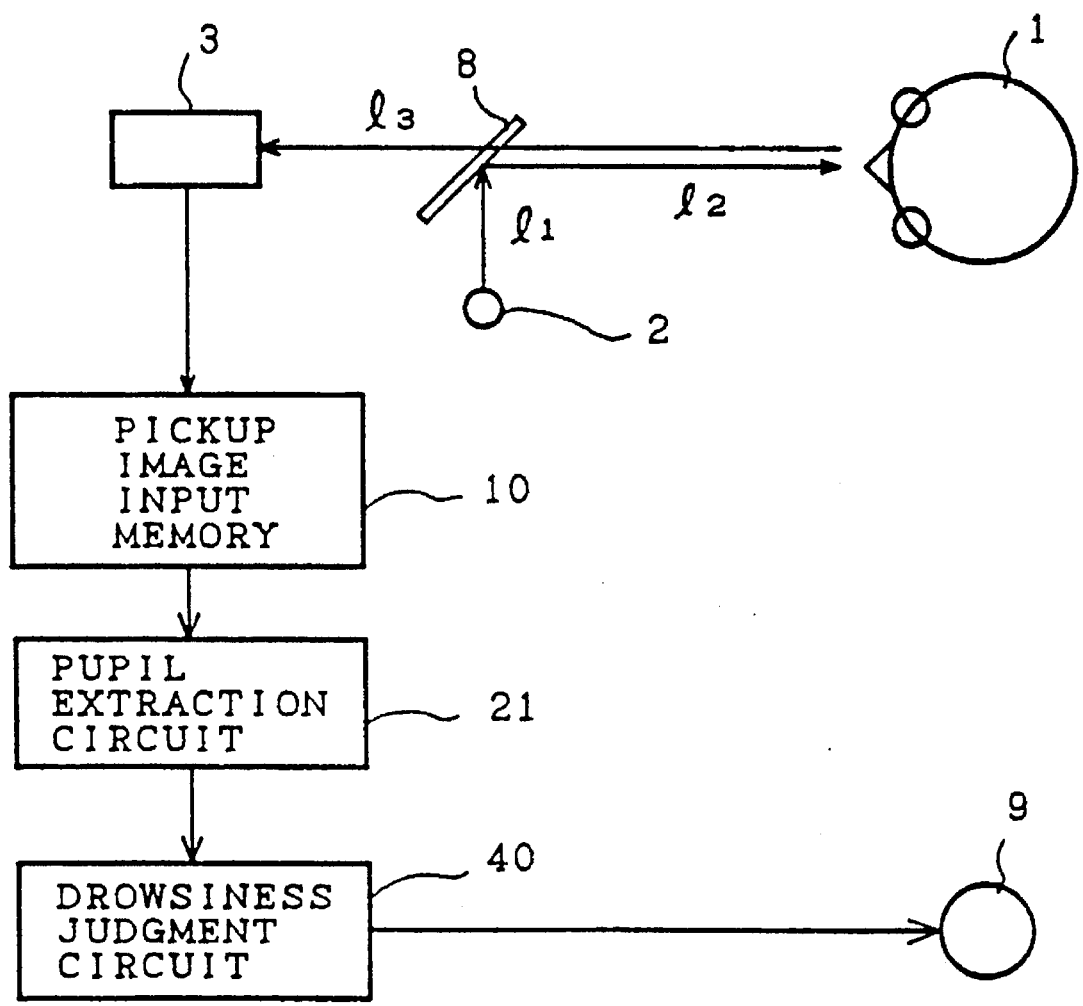
FIG. 3 is a schematic view of a bodily state detection apparatus practiced as a first embodiment of the invention.
Figure 4:
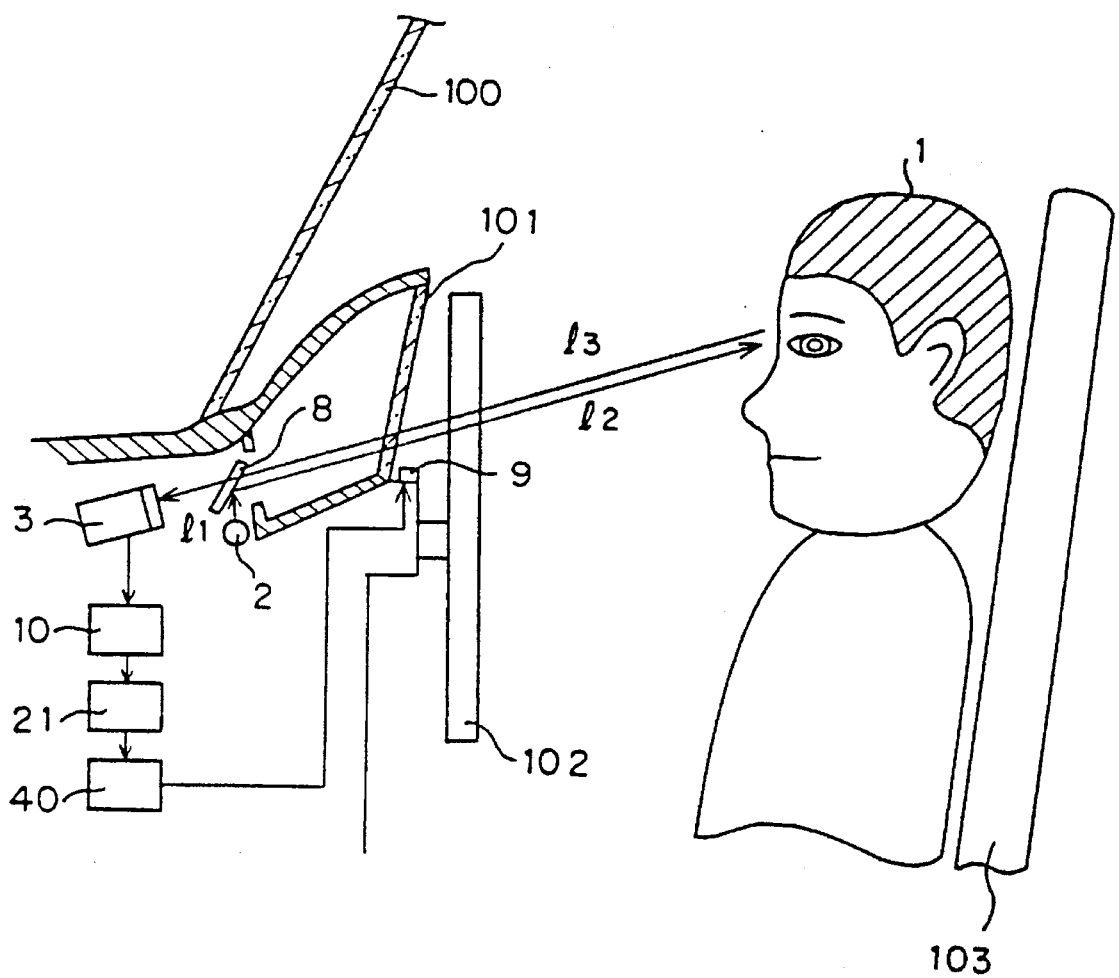
FIG. 4 is a view showing how the first embodiment is mounted illustratively on a vehicle.

FIG. 3 is a schematic view of a bodily state detection apparatus practiced as the first embodiment of the invention. In FIG. 3, reference numeral 3 is a CCD camera (i.e., optical input means) so positioned as to pick up images of a predetermined area including the face of a subject person 1, and 2 is illumination means such as an infrared LED device for illuminating the subject person 1. Illustratively, the center illumination wavelength of the infrared LED device 2 is 860 nm and its radiation direction characteristic is ±20°. Reference numeral 8 is a half mirror; 9 is a buzzer; 10 is a pickup image input memory that temporarily stores the output data of the CCD camera 3; 21 is a pupil extraction circuit that extracts pupil data from the pickup image input memory 10; and 40 is a drowsiness judgment circuit that checks to see if the subject person 1 is drowsy, the check being performed by detecting the eyelid movement based on the data from the pupil extraction circuit 21. The apparatus of the structure outlined in FIG. 3 is used advantageously with a nighttime image pickup device. FIG. 4 is a schematic view depicting how the first embodiment is mounted illustratively on a vehicle. In FIG. 4, reference numeral 100 is the windshield; 101 is a transparent cover on the instrument panel; 102 is the steering wheel; and 103 is the driver's seat. Deep inside the instrument panel are the half mirror 8, the LED device 2 and the CCD camera 3. The buzzer 9 is located on the shaft of the steering wheel 102.

Figure 5:
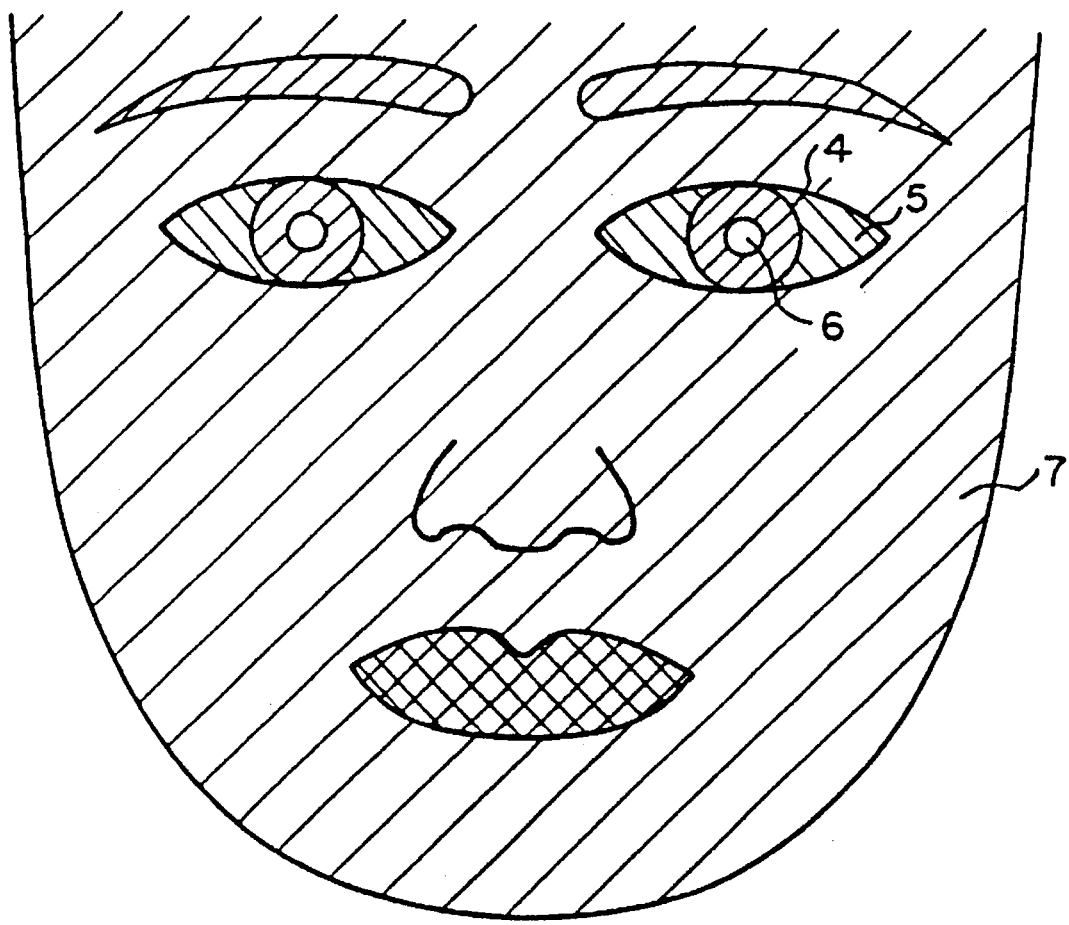
FIG. 5 is a view of a pickup image taken by optical input means of the first embodiment.
Figure 6A:
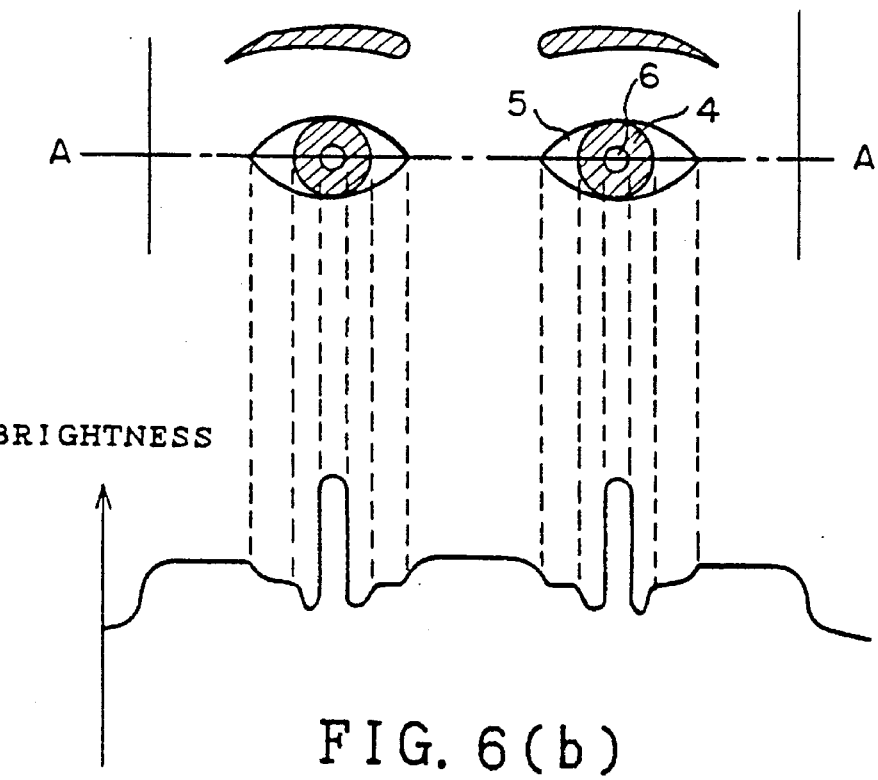
FIGS. 6(a) and 6(b) are views of pickup images compared with each other, one taken by the optical input means of the first embodiment, the other taken by the conventional apparatus.
Figure 6B:
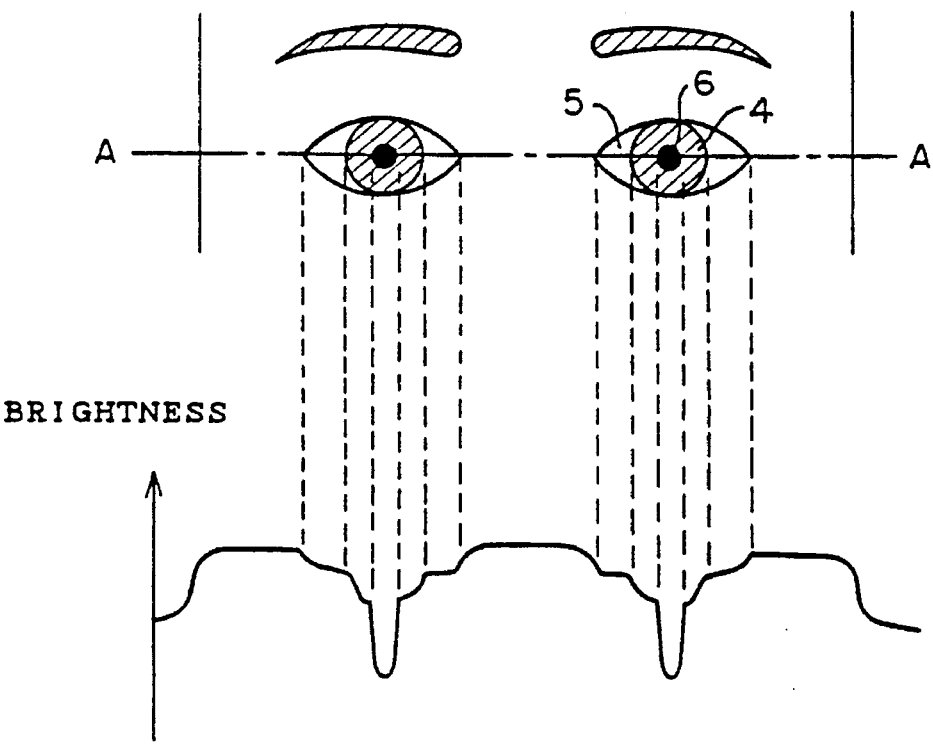
Figure 7:
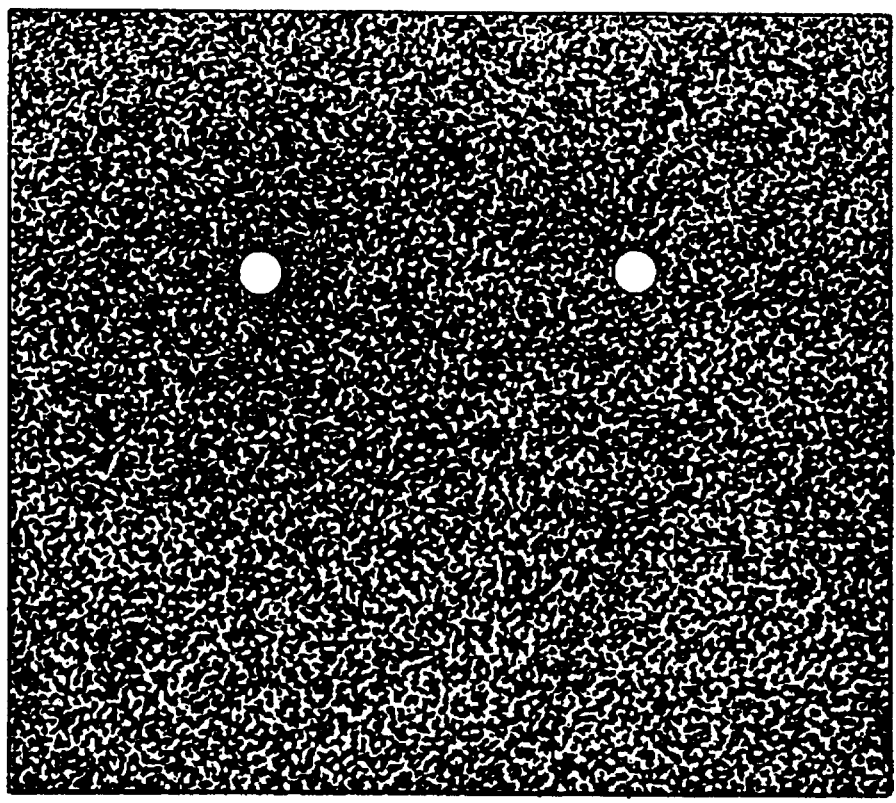
FIG. 7 is a view depicting the result of pupil extraction performed by a pupil extraction circuit of the first embodiment.

In operation and referring to FIG. 3, illumination from the infrared LED device 2 travels along an optical path 11. Half of the illumination is reflected by the half mirror 8 to illuminate the face of the subject person 1 in an optical path 12. An image of the subject person 1 passes through the half mirror 8 along an optical path 13, half of the light reaching the CCD camera 3 which picks up the image of the subject person 1. In this setup, the optical axis of the optical path 12 and that of the optical path 13 are substantially coaxial or fall within a predetermined angle (2 degrees) as viewed from the subject person 1 (the so-called coaxial illumination). With the first embodiment, the predetermined angle is 0; the angle of the half mirror 8 relative to the optical axis 13 of the CCD camera 3 is 45 degrees. The image thus taken of the subject person 1 is shown illustratively in FIG. 5. In FIG. 5, the above-described coaxial illumination setup causes the retinal reflection to make the pupils 6 apparently flash; the pupils appear significantly brighter than the other facial regions and feature points. This is because the retina tends to return the reflection of the incident light in the same direction in which the latter came. FIGS. 6(a) and 6(b) depict typical patterns of brightness distribution in pickup images. The image in FIG. 6(a) is taken by the first embodiment and that in FIG. 6(b) by the conventional apparatus. Comparing the two images reveals that the image taken by the first embodiment has a distinctly high degree of brightness in the pupil position compared with other regions of the image. This means that a binary image of FIG. 7 is obtained through simple binary threshold adjustment (i.e., bright or not bright) of the pickup image. The binary image has two encircled white regions representing the subject person's pupils against the dark background. The position and the shape of the pupils are easy to detect from this binary image through simple calculations such as those for finding the center of gravity; there is no need for conventionally required complicated computations.

Figure 8:
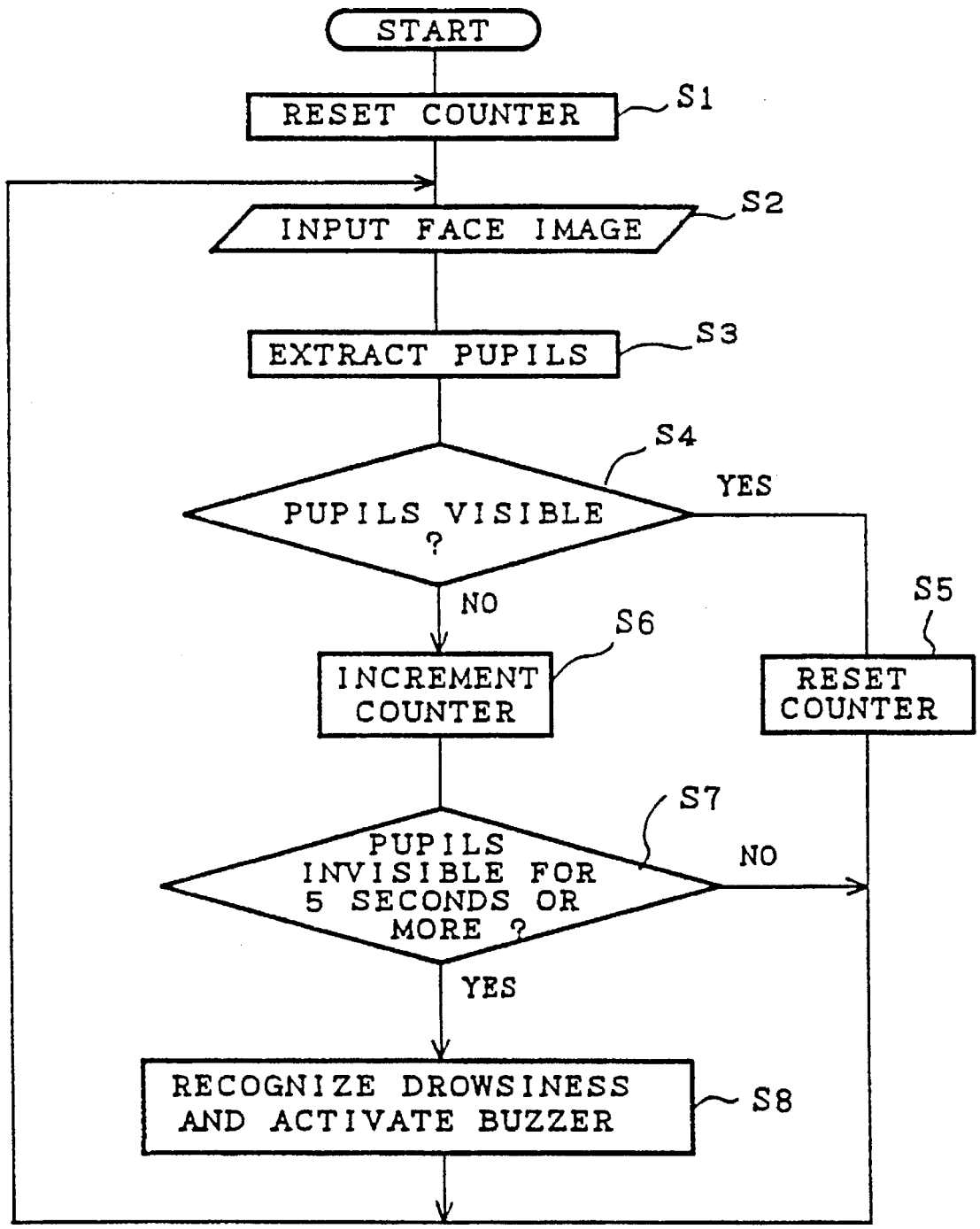
FIG. 8 is a flowchart of steps in which the first embodiment operates.

How the first embodiment detects the subject person's drowsiness will now be explained with reference to FIG. 8. In step 1, a counter is reset. In step 2, a face image is input. In step 3, the face image is subjected to binary processing (i.e., bright or not bright) whereby the pupils are extracted from the image. With the pupils so extracted, step 4 is reached in which a check is made to see if the pupils are visible. If the pupils are visible, step 5 is reached in which the counter is reset, and step 2 is reached again. If the pupils are not visible in step 4, step 6 is reached in which the counter is incremented. In step 7, a check is made to see if the pupils are invisible for five seconds or more (counter value: 5000/33=167). If the pupils are invisible for five seconds or more, the subject person is judged to be drowsy and step 8 is reached. In step 8, the buzzer is activated. If the pupils are invisible for less than five seconds in step 7, step 2 is reached again.

Although the illumination means 20 of the first embodiment is the infrared LED device, it may be replaced by a halogen lamp that generates broad-band wave-length light in a manner less affected by temperature fluctuation. Alternatively, the illumination means 20 may comprise a halogen lamp and a filter that spectrally filters the generated light on specific waveforms. The camera, being of CCD type in the first embodiment, may alternatively be a CID (charge injection device) camera.

Second Embodiment

Figure 9:
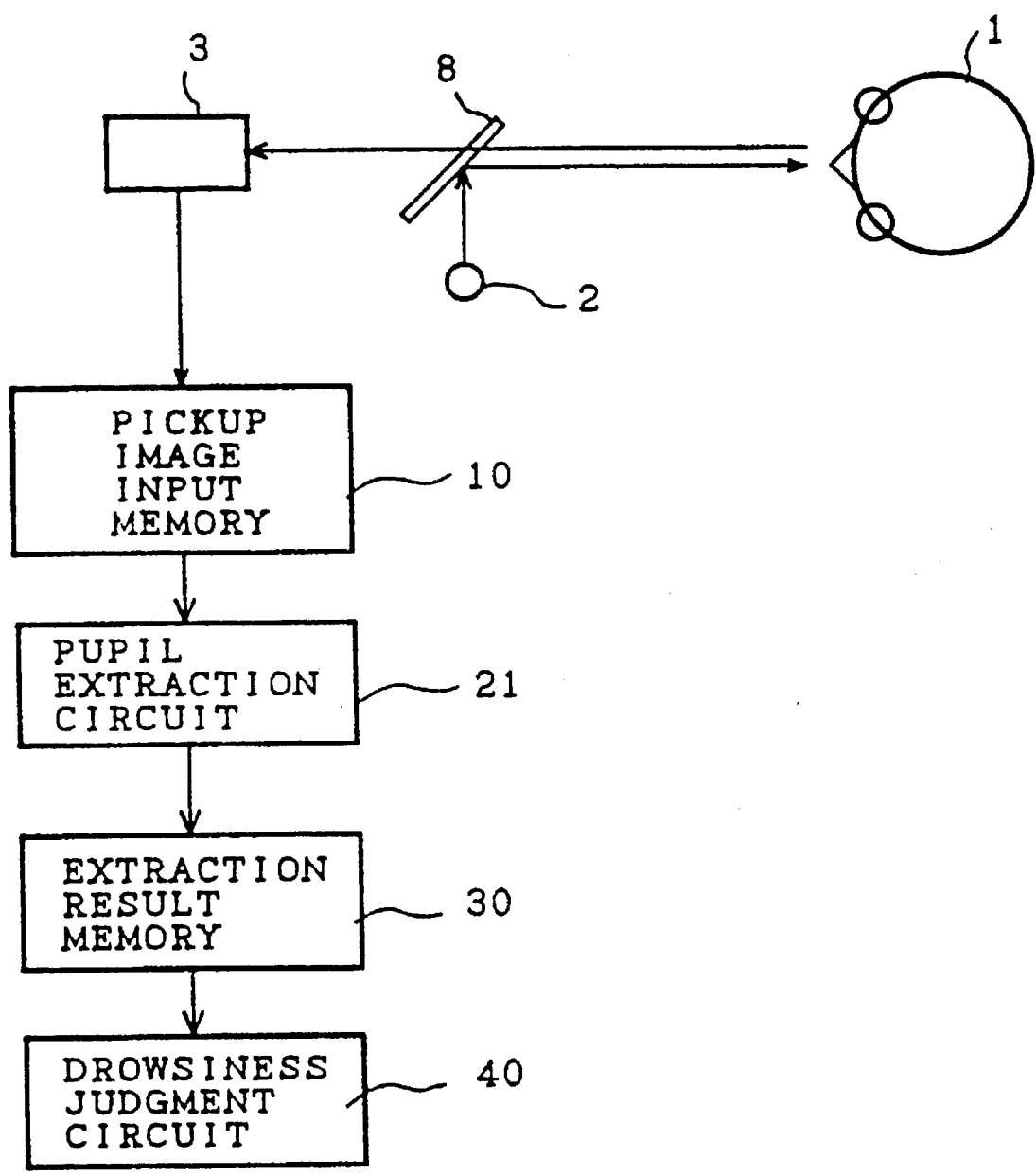
FIG. 9 is a schematic view of a bodily state detection apparatus practiced as a second embodiment of the invention.

FIG. 9 is a schematic view of a bodily state detection apparatus in a preferred structure according to the second embodiment of the invention. Whereas the first embodiment has judged the subject person's drowsiness (degree of alertness) in accordance with the visibility of that person's pupils, the second embodiment passes a judgment on the subject person's degree of alertness on the basis of the time series data about the pupil position. That is, drowsiness is deduced from the fact that the person in a drowsy state becomes gradually "downcast" and his apparent pupil position becomes lower. In FIG. 9, reference numeral 30 is an extraction result memory that stores pupil positions extracted by the pupil extraction circuit 21. A drowsiness judgment circuit 40 determines the subject person's drowsiness according to the duration in which that person's face remains downcast, the duration being determined from the time series data about the pupil positions stored in the extraction result memory 30.

Figure 10:
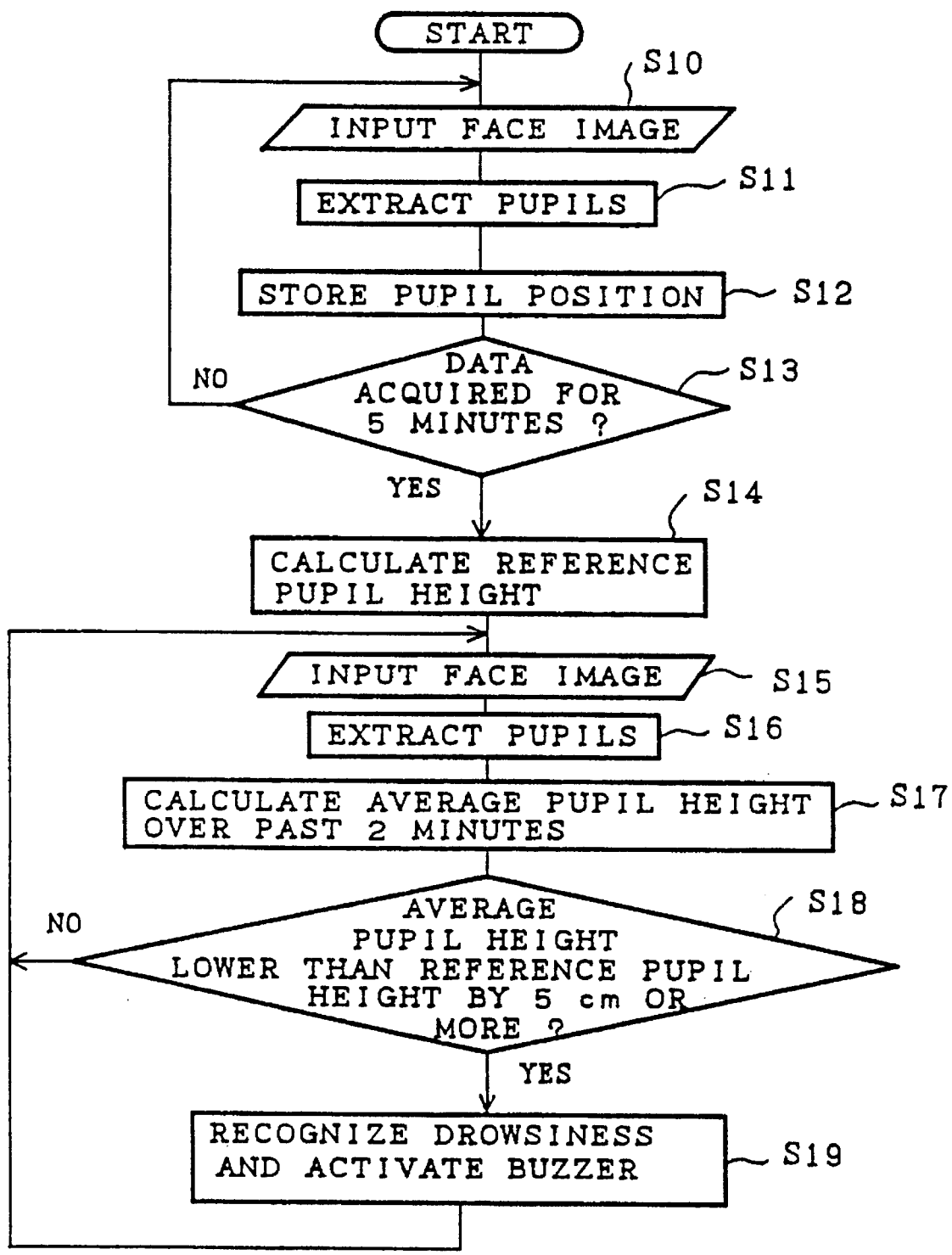
FIG. 10 is a flowchart of steps in which the second embodiment operates.

How the second embodiment works will now be described with reference to the flowchart of FIG. 10. In step 10, a face image is input. In step 11, the face image is subjected to binary processing (i.e., bright or not bright) as with the first embodiment, whereby the pupils are extracted from the image. In step 12, the position of the extracted pupils (i.e., pupil height) is stored. In step 13, a check is made to see if the data about the pupils has been gathered for five minutes or more. If the data has been collected at least over the past five minutes, step 14 is reached. In step 14, the pupil heights over the first five minutes are averaged and a reference pupil height (T1) is calculated. After the five minutes, another face image is input in step 15. In step 16, the pupils are extracted from the face image. In step 17, the pupil heights over the past two minutes are averaged. In step 18, a check is made to see if the average pupil height is lower than the reference pupil height by a predetermined value (5 cm for the second embodiment). If the average pupil height is found to be lower than the reference pupil height by 5 cm or more, step 19 is reached. In step 19, the subject person's continuous "downcast" state is interpreted as a dangerous drop in that person's alertness (i.e., drowsy state). FIG. 11(a) is a graphic representation of time series data about pupil positions, and FIG. 11(b) is a graphic representation of time series data about average pupil positions. In FIGS. 11(a) and 11(b), $t_1$ represents the time that elapses before the reference pupil position is acquired, T1 denotes the reference pupil position so obtained, and $t_2$ is the time at which the subject person's drowsiness is detected.

Because the second embodiment utilizes time series information about the subject person's pupils, the embodiment activates the buzzer before that person is asleep. With the degree of the subject person's drowsiness detected before it is too late, the second embodiment improves the quality of drowsiness detection.

Instead of the reference pupil position being fixed at its initial value, the position may alternatively be updated at intervals of a time (e.g., 30 minutes) longer than the time (2 minutes) in which to find the pupil position.

Third Embodiment

Figure 12:
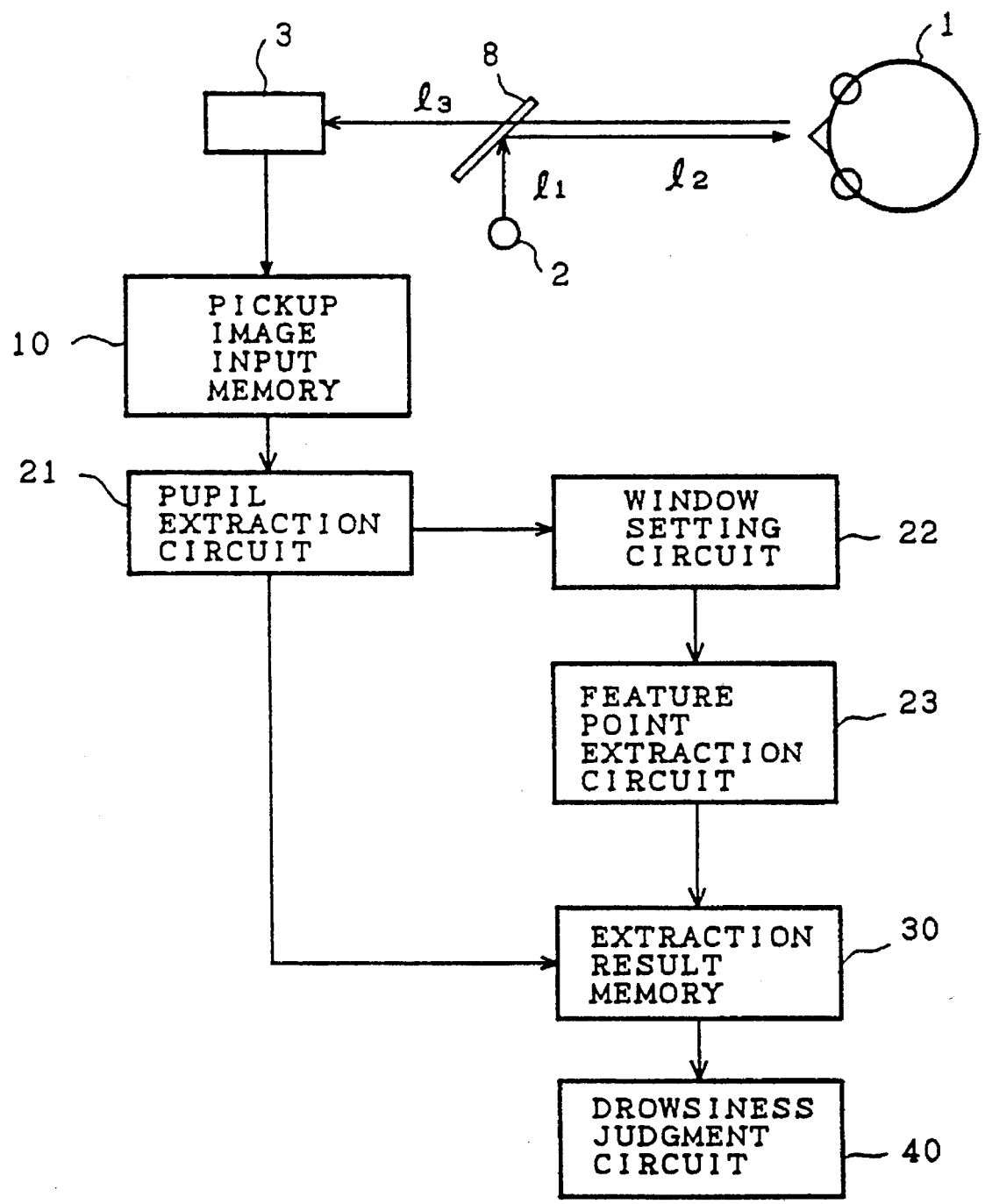
FIG. 12 is a schematic view of a bodily state detection apparatus practiced as a third embodiment of the invention.

FIG. 12 is a schematic view of a bodily state detection apparatus in a preferred structure according to the third embodiment of the invention. Whereas the second embodiment has judged the subject person's drowsiness based on the pupil positions detected, the third embodiment detects other feature points of that person's face to acquire the face feature quantities in a more direct manner. This ability allows the third embodiment to offer higher accuracy in bodily state detection. In FIG. 12, reference numeral 22 is a window setting circuit (search range definition means) that defines the range (window) of search for other facial feature points such as the nostrils with respect to the pupil position extracted by the pupil extraction circuit 21. A feature point extraction circuit 23 extracts the position or shape of the feature points from inside the window defined by the window setting circuit 22. For example, a window measuring 6×6 cm is set around a position 5 cm below the middle point between the two pupils. Image processing is carried out within that window to search for and find the nostrils. Illustratively, the target nostrils to be searched for should each be 1 cm across or less and appear with low brightness. An extraction result memory 30 stores the pupil positions obtained by the pupil extraction circuit 21 as well as the nostril positions acquired by the feature point extraction circuit 23. A drowsiness judgment circuit 40 finds the face inclination from the apparent positional relationship between the nostrils and the two pupils. With the subject person's "downcast" time obtained, the drowsiness judgment circuit 40 judges that person to be drowsy as per an appropriate benchmark of the downcast state duration.

How the third embodiment works to detect the subject person's drowsiness will now be described. The pupil positions obtained by the pupil extraction circuit 21 and the nostril positions acquired by the feature point extraction circuit 23 are stored in the extraction result memory 30. As with the second embodiment, the data over the initial five minutes is illustratively used to find an apparent distance S0 between the midpoint between the pupils on the one hand, and the midpoint between the nostrils on the other, as the subject person faces the front. Thereafter, the data over the next two minutes is illustratively used to find another apparent distance S between the midpoint between the pupils on the one hand, and the midpoint between the nostrils on the other. The tilt angle θ of the subject person's face is obtained from the distances S0 and S thus acquired. Specifically, the apparent distance S in effect when the face is downcast by the angle a is given as $$S = S0 \cdot \cos(\theta)$$

When the average face tilt angle θ obtained in two minutes becomes illustratively 20 degrees or more, the subject person is judged to be drowsy.

Compared with the second embodiment, the third embodiment distinguishes two cases of the subject person's bodily state: one in which only the pupil height moves up and down, and the other in which the entire face tilts. This ability allows the third embodiment to provide higher levels of accuracy in drowsiness detection than the second embodiment.

Although the third embodiment obtains the apparent distance S0 from the subject person's initial state, a message may be issued alternatively to that person asking him to face the front before the distance S0 is acquired.

The third embodiment utilizes the extraction result memory 30 to accommodate the data averaged over two or five minutes. Alternatively, the extraction result memory 30 may be removed and there may be provided means for detecting the momentary face orientation of the subject person.

Fourth Embodiment

Figure 13:
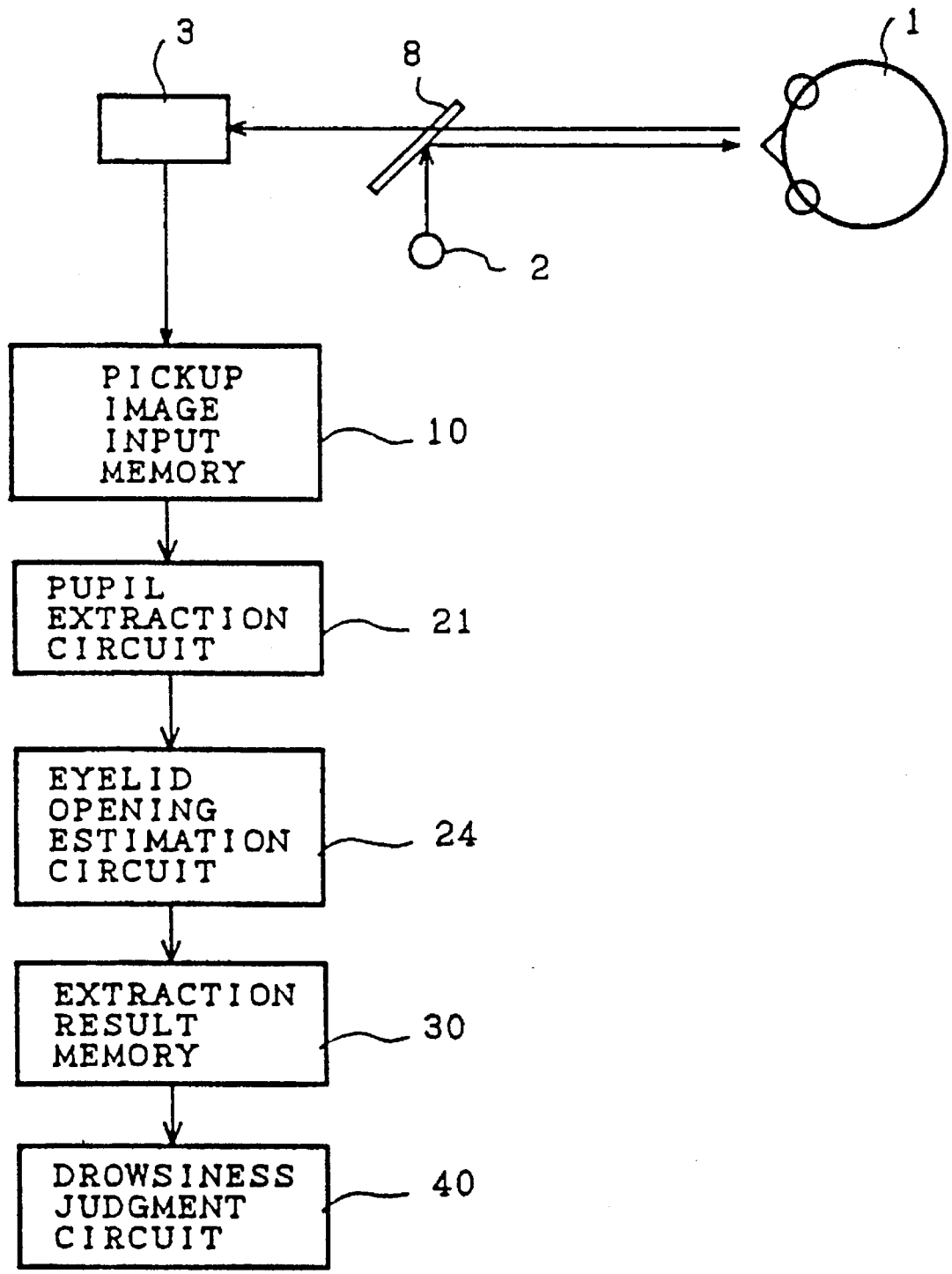
FIG. 13 is a schematic view of a bodily state detection apparatus practiced as a fourth embodiment of the invention.

FIG. 13 is a schematic view of a bodily state detection apparatus in a preferred structure according to the fourth embodiment of the invention. The fourth embodiment estimates the degree of eyelid opening by finding the ratio of the vertical length to the horizontal length of the subject person's pupils, thereby detecting the half-closed state of that person's eyelids. In FIG. 13, reference numeral 24 is an eyelid opening estimation circuit that estimates the degree of eyelid opening from the pupil shape extracted by the pupil extraction circuit 21; 30 is an extraction result memory that stores the degree of eyelid opening so estimated; and 40 is a drowsiness judgment circuit that judges the subject person's drowsiness on the basis of the duration of the half-closed state of that person's eyelids.

The fourth embodiment works to detect the subject person's drowsiness as follows: the pupil extraction circuit 21 first extracts the pupil shape. Given the pupil shape, the eyelid opening estimation circuit 24 finds the apparent vertical length y and the apparent horizontal length x of the subject person's pupil. From the ratio of the vertical length to the horizontal length (y/x), the eyelid opening estimation circuit 24 estimates the degree of eyelid opening. FIGS. 14(a), 14(b), and 14(c) show how the eyelids are opened and closed. It can be seen from the figures that as the eyelids are getting closed, the ratio y/x becomes smaller. The extraction result memory 30 stores the degrees of eyelid opening y/x thus acquired. If the ratio y/x is, say, ½ or less, the drowsiness judgment circuit 40 judges the eyelids to be in a half-closed state. When the half-closed state of the eyelids lasts two minutes or longer, the subject person is judged to be drowsy. As with the second and third embodiments, the ratio y/x in the first five minutes may alternatively be averaged. Then if the current ratio y/x becomes ½ or less of the initially averaged ratio, the eyelids are judged to be in a half-closed state. When the half-closed state of the eyelids continues two minutes or longer, the subject person is judged to be drowsy.

As described, the fourth embodiment estimates the degree of eyelid opening from the pupil shape. With the blinking state of the subject person thus recognized as in the case of the second embodiment, the fourth embodiment detects a dangerous drop in that person's degree of alertness and thereby enhances the quality of drowsiness detection.

Fifth Embodiment

Figure 15:
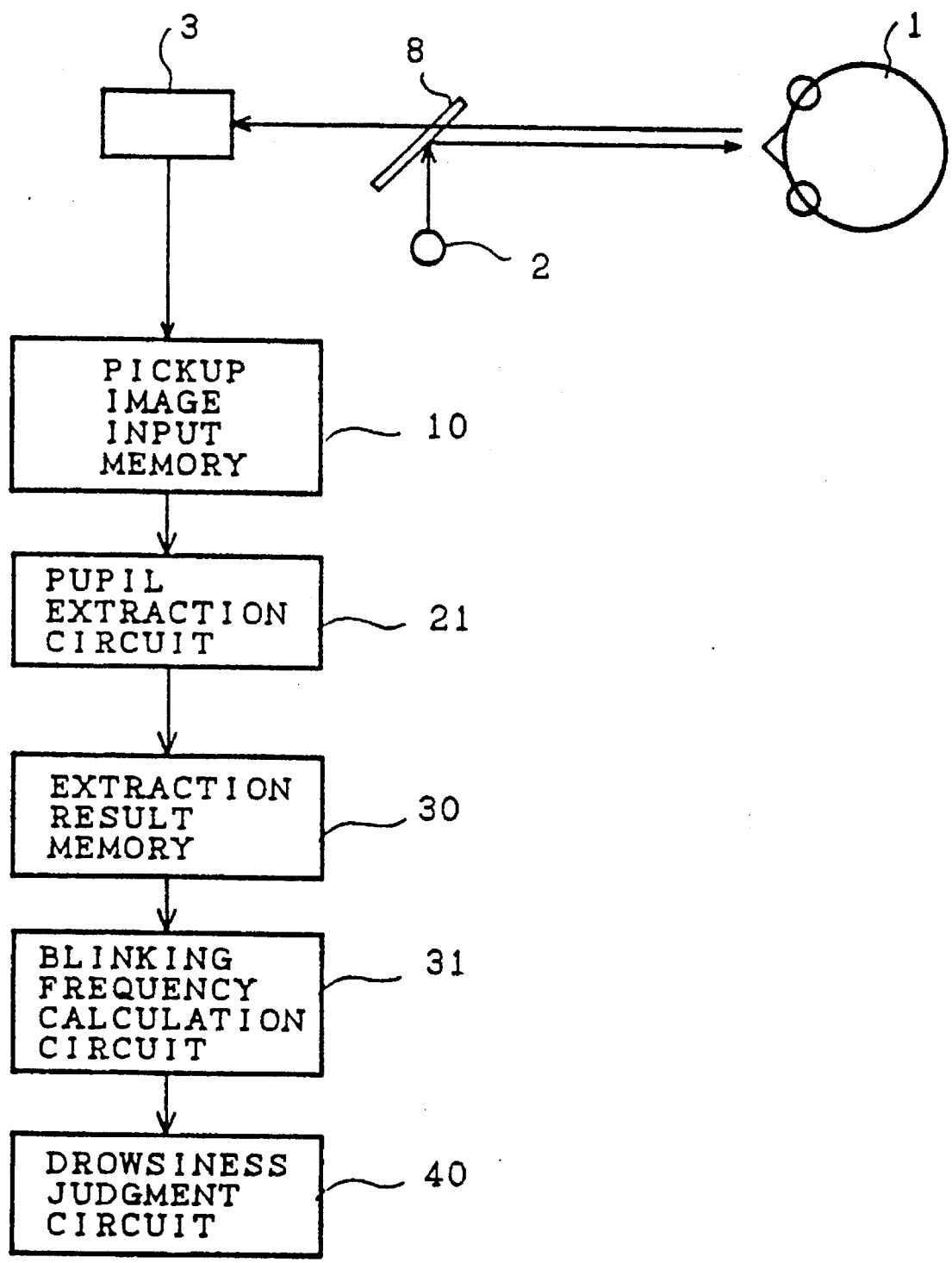
FIG. 15 is a schematic view of a bodily state detection apparatus practiced as a fifth embodiment of the invention.

FIG. 15 is a schematic view of a bodily state detection apparatus in a preferred structure according to the fifth embodiment of the invention. The fifth embodiment estimates the subject person's blinking frequency on the basis of that person's pupil area. With the blinking frequency so estimated, the embodiment detects the subject person's drowsiness. In FIG. 15, reference numeral 21 is a pupil extraction circuit that extracts the pupil shape from the pickup image and counts the number of picture elements involved to find the pupil area; 30 is an extraction result memory that stores the pupil areas acquired by the pupil extraction circuit 21 at intervals of, say, 10 ms; and 31 is a blinking frequency calculation circuit that turns the time series data about the pupil areas into binary data as per a threshold value, thereby calculating the subject person's blinking frequency. Reference numeral 40 represents a drowsiness judgment circuit that determines the subject person's drowsiness according to that person's blinking frequency so calculated.

Figure 16A:
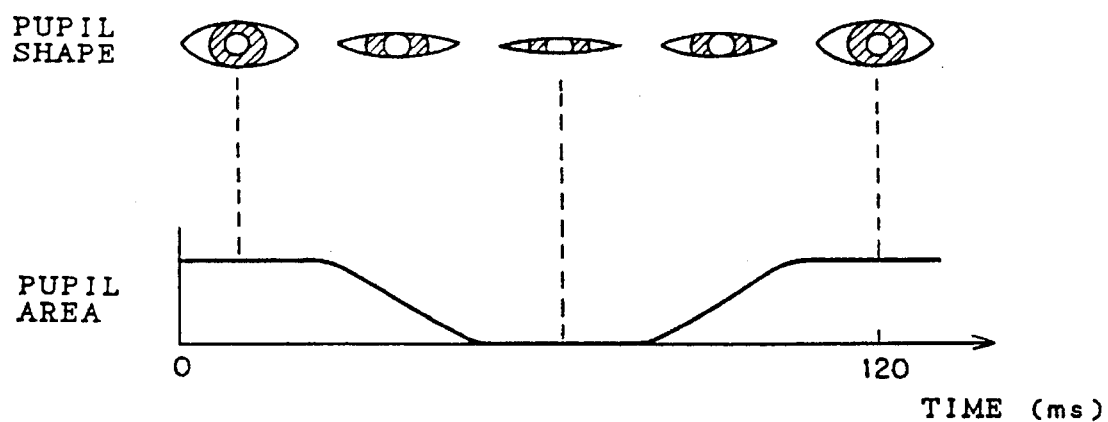
FIGS. 16(a) and 16(b) are graphic representations showing how the fifth embodiment works illustratively.
Figure 16B:
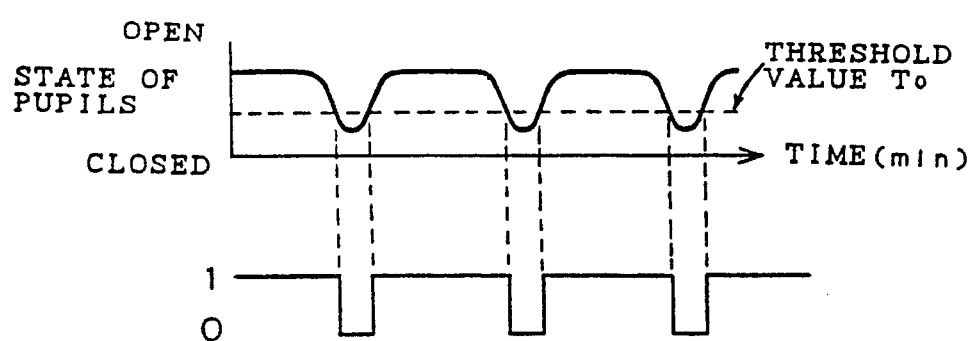

How the fifth embodiment works will now be described with reference to FIGS. 16(a) and 16(b). FIG. 16(a) is a graphic representation indicating changes in the subject person's pupil area in effect when that person blinks. These changes are acquired by counting the number of the picture elements constituting the pupil. The extraction result memory 30 accommodates the pupil areas obtained by the pupil extraction circuit 21 at intervals of 10 ms. FIG. 16(b) is a graphic representation of typical time series data denoting the blinks. The blinking frequency calculation circuit 31 turns the time series data into binary data of 0's and 1's using a threshold value T. For example, the subject person's blinking frequency is calculated by counting the number of "0" regions gathered in two minutes. A typical relationship between blinking frequencies and degrees of alertness is shown in FIGS. 17(a) and 17(b). As illustrated, the blinking frequency is about 10 times per minute when the degree of alertness is high. As the alertness drops, the blinking frequency increases. When the subject person's blinking frequency is 20 times per minute or more, that person is judged to be drowsy.

As described, the fifth embodiment estimates the subject person's blinking frequency based on the pupil shape. With the blinking state determined as in the case of the fourth embodiment, the fifth embodiment detects a dangerous drop in the subject person's alertness and thus enhances the quality of drowsiness detection.

The threshold value of the blinking frequency may be other than 20. Alternatively, the blinking frequencies in effect when the subject person's degree of alertness is high may be averaged. When the subject person's current blinking frequency becomes, say, twice the average blinking frequency so obtained, that person may be judged to be drowsy.

Whereas the fifth embodiment detects the subject person's drowsiness, it is known that the blinking frequency increases when the person is bored and drops when he is excited. Thus changes in the subject person's blinking frequency may be monitored so as to detect that person's mental states such as excitement and tenseness.

Sixth Embodiment

Figure 18:
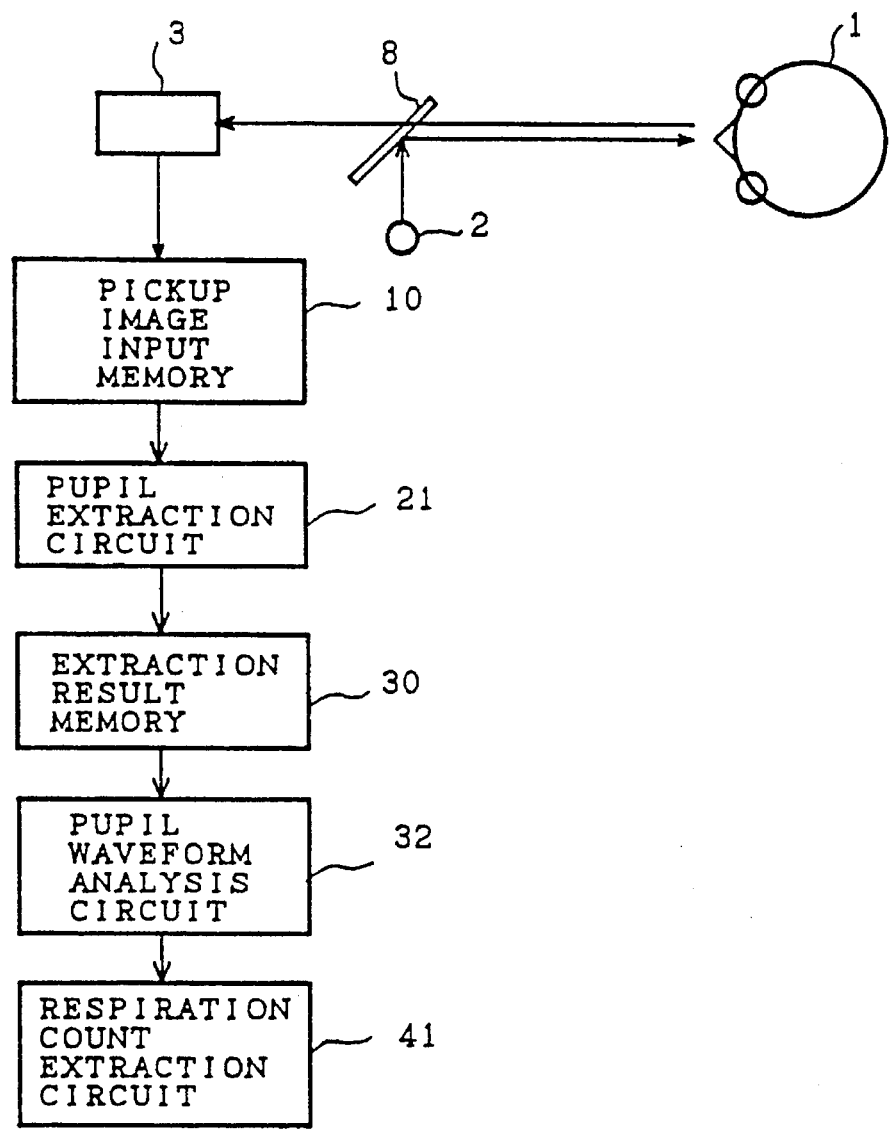
FIG. 18 is a schematic view of a bodily state detection apparatus practiced as a sixth embodiment of the invention.
Figure 19:
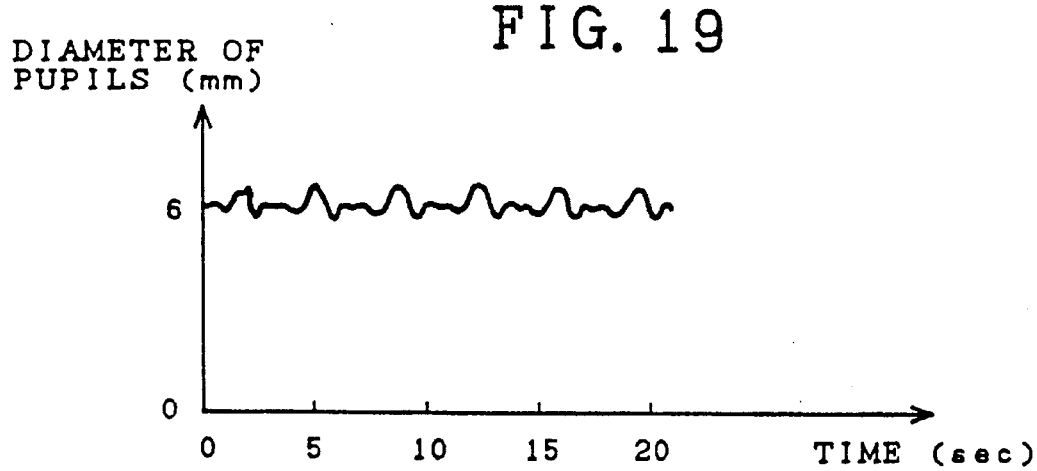
FIG. 19 is a graphic representation showing how the sixth embodiment works illustratively.
Figure 20:
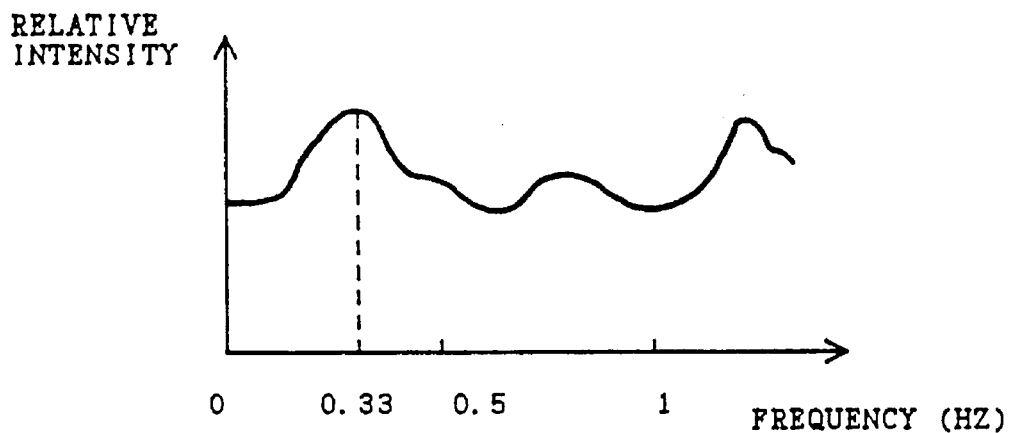
FIG. 20 is another graphic representation depicting how the sixth embodiment works illustratively.

FIG. 18 is a schematic view of a bodily state detection apparatus in a preferred structure according to the sixth embodiment of the invention. The sixth embodiment measures the diameter of the subject person's pupils so as to detect the degree of expansion and contraction of that person's pupils and to determine his respiration cycle. In FIG. 18, reference numeral 21 is a pupil extraction circuit that extracts the subject person's pupil shape and measures the diameter of the pupils, and 30 is an extraction result memory that stores the pupil diameters acquired by the pupil extraction circuit 21 at intervals of, say, 10 ms. A pupil waveform analysis circuit 32 performs frequency analysis of the pupil waveform plotted illustratively as shown in FIG. 19. A respiration count extraction circuit 41 determines the current respiration count based on the result of the frequency analysis such as is shown in FIG. 20, performed by the pupil waveform analysis circuit 32.

The sixth embodiment works to detect the respiration count as follows: when observed closely, the pupils are seen vibrating in a minute manner as illustrated in FIG. 19. Of the components constituting the fluctuating waveform thus observed, those of low frequencies are known to vary in accordance with the respiration count. FIG. 20 plots results of the frequency analysis performed on what is shown in FIG. 19. As shown in FIG. 20, a peak appears at 0.33 Hz, which corresponds to a respiration cycle of 20 times per minute.

The sixth embodiment takes advantage of the above-described characteristic and determines the respiration count by monitoring changes in the pupil diameter. The pupil extraction circuit 21 extracts the shape and the diameter of the pupils. The extraction result memory 30 stores the pupil diameters at intervals of 10 ms. The pupil waveform analysis circuit 32 performs frequency analysis of the waveform of pupil fluctuations once every minute. Given the result of the analysis, the respiration count extraction circuit 41 searches for and finds a peak in the target range of respiration frequencies, whereby the current respiration count is acquired.

Figure 21:
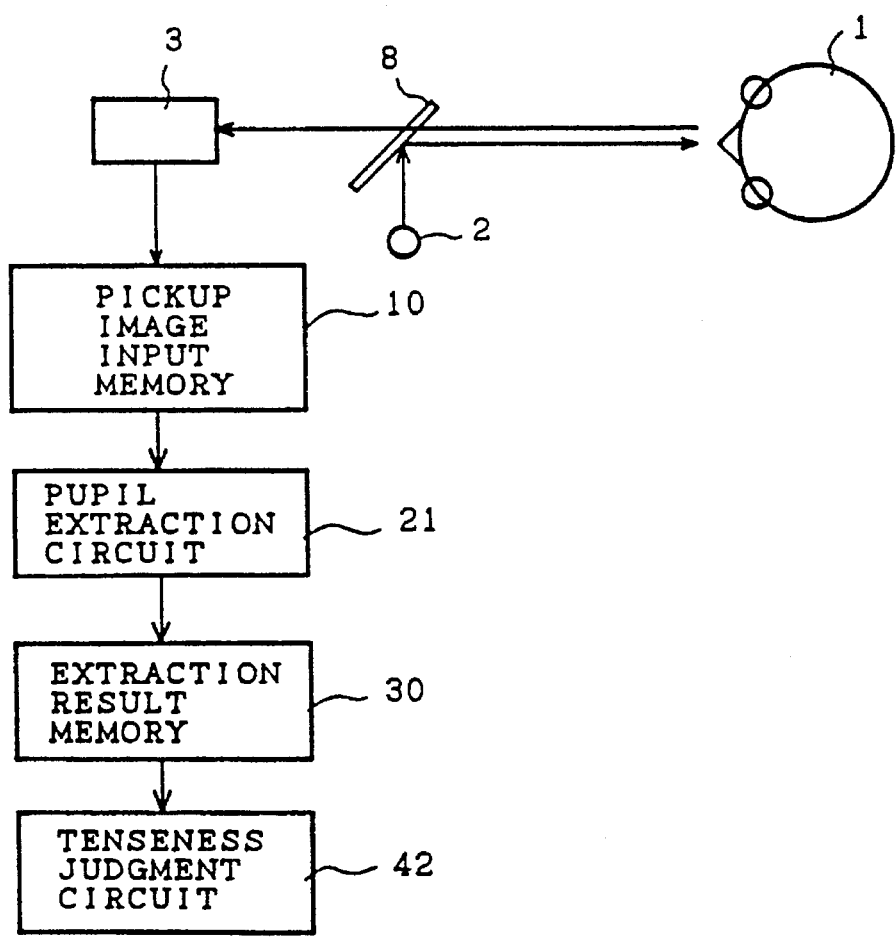
FIG. 21 is a schematic view of a bodily state detection apparatus practiced as a seventh embodiment of the invention.

Whereas the sixth embodiment obtains the respiration count alone, another judgment circuit may be provided alternatively to find the subject person's degree of tenseness or that person's unhealthy state based on the fact that the respiration count increases in proportion to rising tenseness.
Seventh Embodiment FIG. 21 is a schematic view of a bodily state detection apparatus in a preferred structure according to the seventh embodiment of the invention. Whereas the sixth embodiment has performed frequency analysis on the time series data about the pupil diameters so as to measure the respiration count, the seventh embodiment finds the average diameter of the pupils in order to judge the subject person's tenseness based on the average pupil diameter so obtained.

Figure 22A:
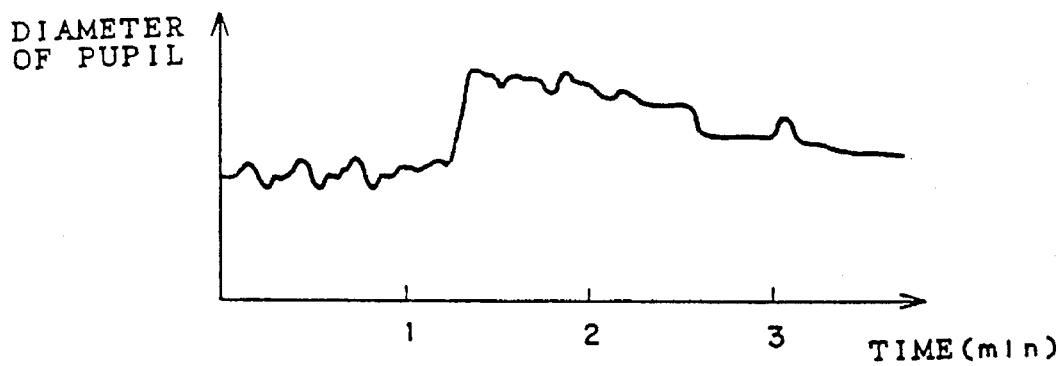
FIGS. 22(a) and 22(b) are graphic representations showing how the seventh embodiment works illustratively.
Figure 22B:
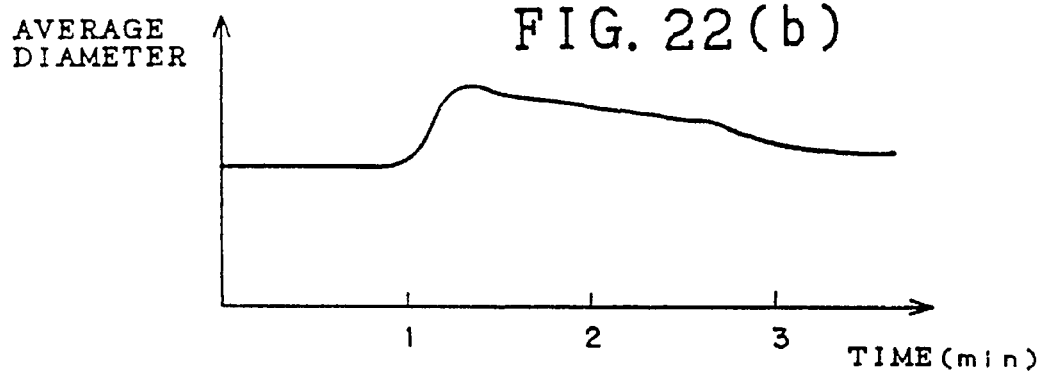
Figure 23A:
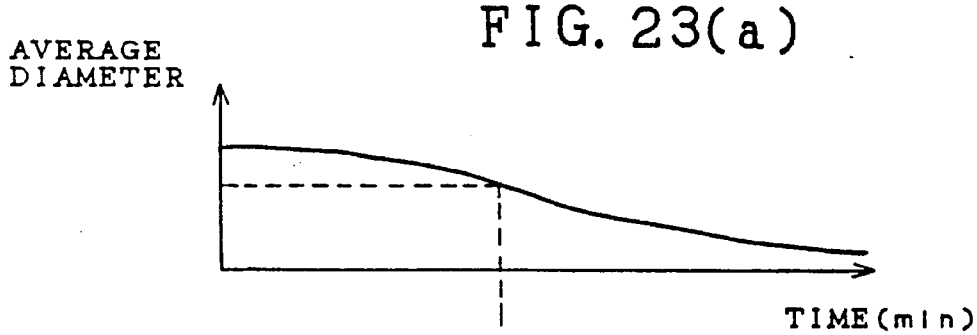
FIGS. 23(a) and 23(b) are another graphic representation depicting how the seventh embodiment works illustratively.
Figure 23B:
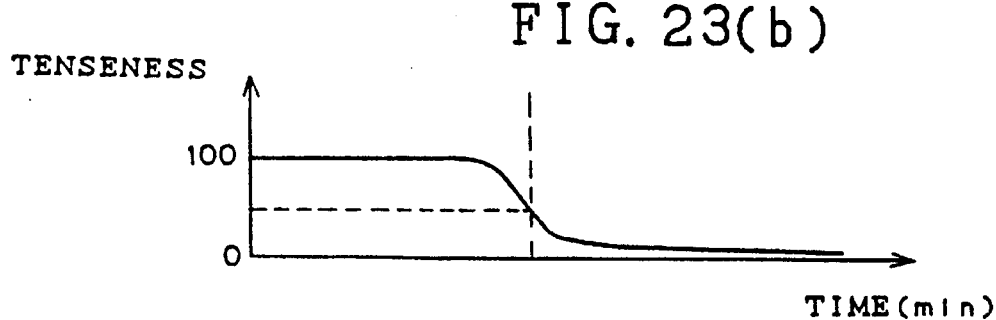

In FIG. 21, reference numeral 21 is a pupil extraction circuit that extracts the shape of the pupils and measures the diameter thereof accordingly; 30 is an extraction result memory that stores the pupil diameters so acquired; and 42 is a tenseness judgment circuit which, having obtained the average diameter, judges that the subject person's tenseness has dropped if the average diameter becomes less than a predetermined value. FIG. 22(a) plots relatively large changes in the pupil diameter over an extended period of time, as opposed to the minute vibrations of the pupil diameter (FIG. 19) detected over a short period of time with the sixth embodiment. When averaged, the changing diameters of the pupils appear as plotted in FIG. 22(b). FIGS. 23(a) and 23(b) illustrate a typical relationship between average pupil diameters and degrees of tenseness. The smaller the average pupil diameter, the lower the degree of tenseness, i.e., the subject person becoming languid.

Figure 24:
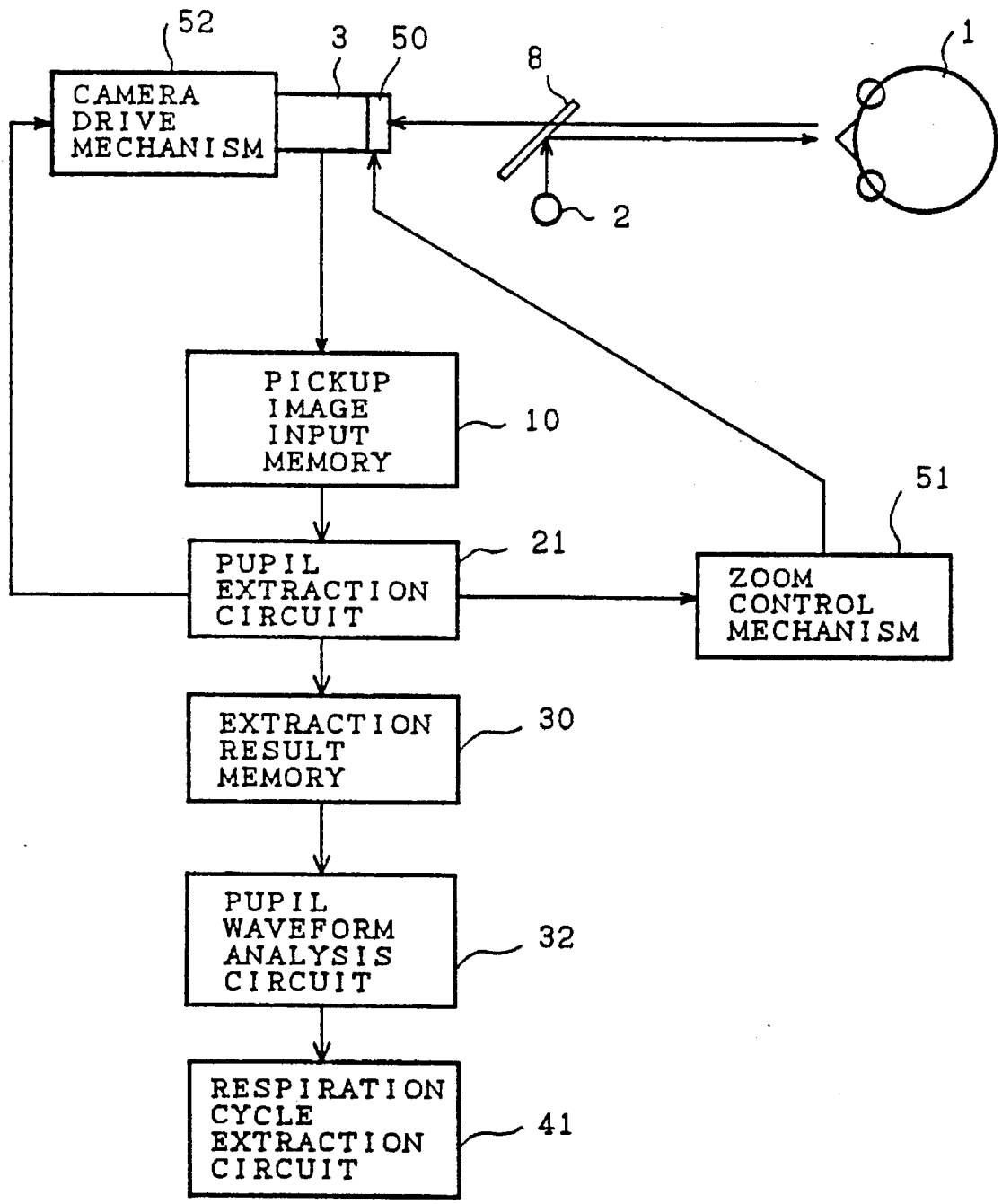
FIG. 24 is a schematic view of a bodily state detection apparatus practiced as an eighth embodiment of the invention.

With the sixth or seventh embodiment, the maximum diameter of the pupils measured from the pupil shape may be taken as the pupil diameter. This makes it possible to evaluate the pupil size correctly regardless of the changing face orientation, whereby the reliability of the embodiment is improved.
Eighth Embodiment FIG. 24 is a schematic view of a bodily state detection apparatus in a preferred structure according to the eighth embodiment of the invention. In FIG. 24, reference numeral 50 is a zoom mechanism that visually magnifies or contracts the face of the subject person 1 before the image of that face is formed on the CCD plane of the CCD camera 3; 51 is a zoom control mechanism that drives the zoom mechanism by interpreting the output signal from the pupil extraction circuit 21; and 52 is a camera drive mechanism that changes the direction of the CCD camera 3. The other components are the same as their counterparts in the sixth embodiment of FIG. 18.

The eighth embodiment works as follows: The pupil diameter is known to be 2 to 8 mm. If the number of picture elements of the CCD camera 3 is 512×512 and if an image 25.6 cm square is taken of the subject person 1, as assumed for the eighth embodiment, the prime number of the pupil diameter is 4 to 16. Therefore, the waveform of pupil fluctuations would be difficult to extract accurately when the pupil diameter is small. This difficulty is bypassed by the eighth embodiment which is a variation of the sixth embodiment supplemented with the zoom mechanism 50. The added mechanism assures that an image of the pupil is taken in a manner magnified around the pupil center. This arrangement allows the embodiment to extract the pupil fluctuation waveform with high accuracy.

When the pupil extraction circuit 21 extracts the pupil position, the camera drive mechanism 52 changes the camera direction so that an image of either of the pupils may be picked up in the camera center. The zoom control circuit 51 then controls the zoom mechanism 50 so as to pick up an image 5.1 cm square of the subject person 1. This makes it possible to take a 5× magnification image of the pupil, whereby the accuracy of extracting the waveform of pupil fluctuations is enhanced.

If the subject person 1 moves slightly, only the direction of the camera 3 is modified to follow that person's movement while the zoom magnification remains unchanged. If the movement of the subject person 1 is too large to follow, the zoom magnification is reduced to 1× so as to detect the pupil again, and then the zooming is resumed.

Figure 25:
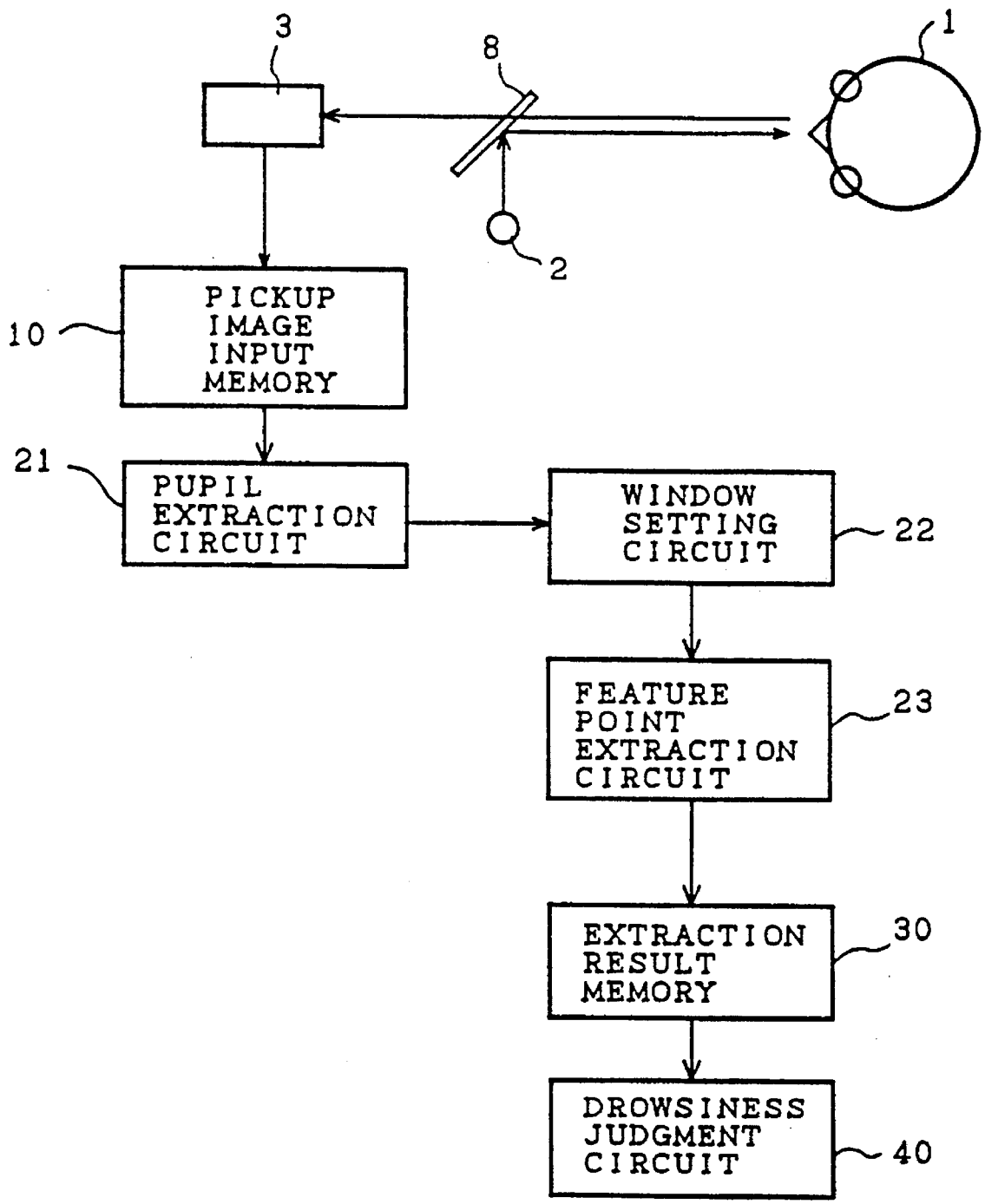
FIG. 25 is a schematic view of a bodily state detection apparatus practiced as a ninth embodiment of the invention.
Figure 26:
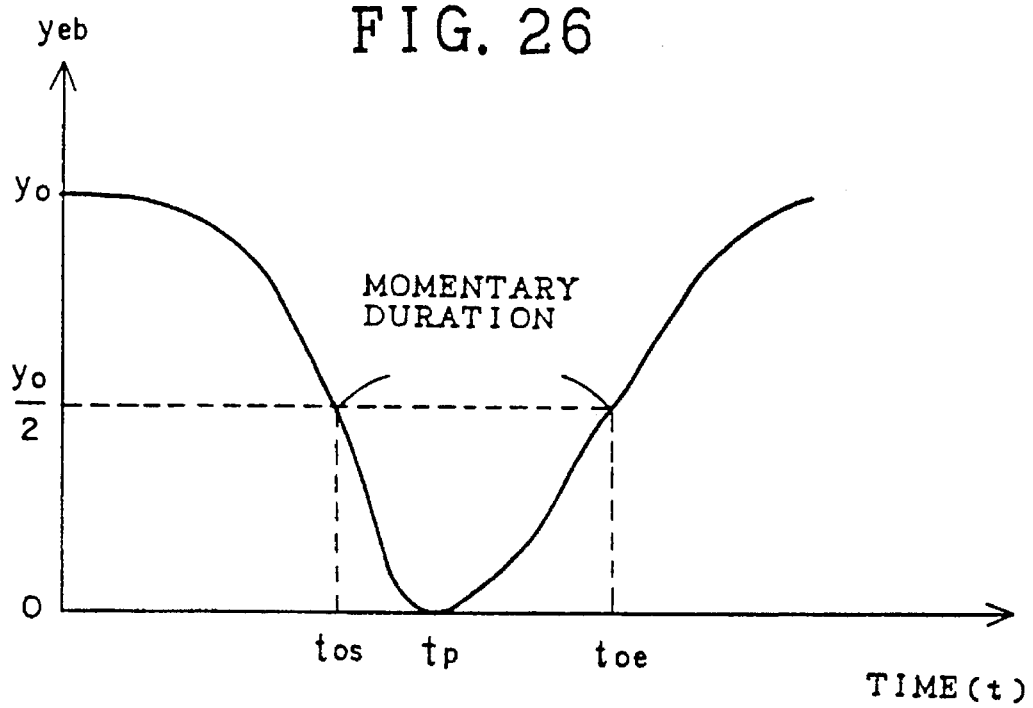
FIG. 26 is a graphic representation showing how the ninth embodiment works illustratively.
Figure 27:
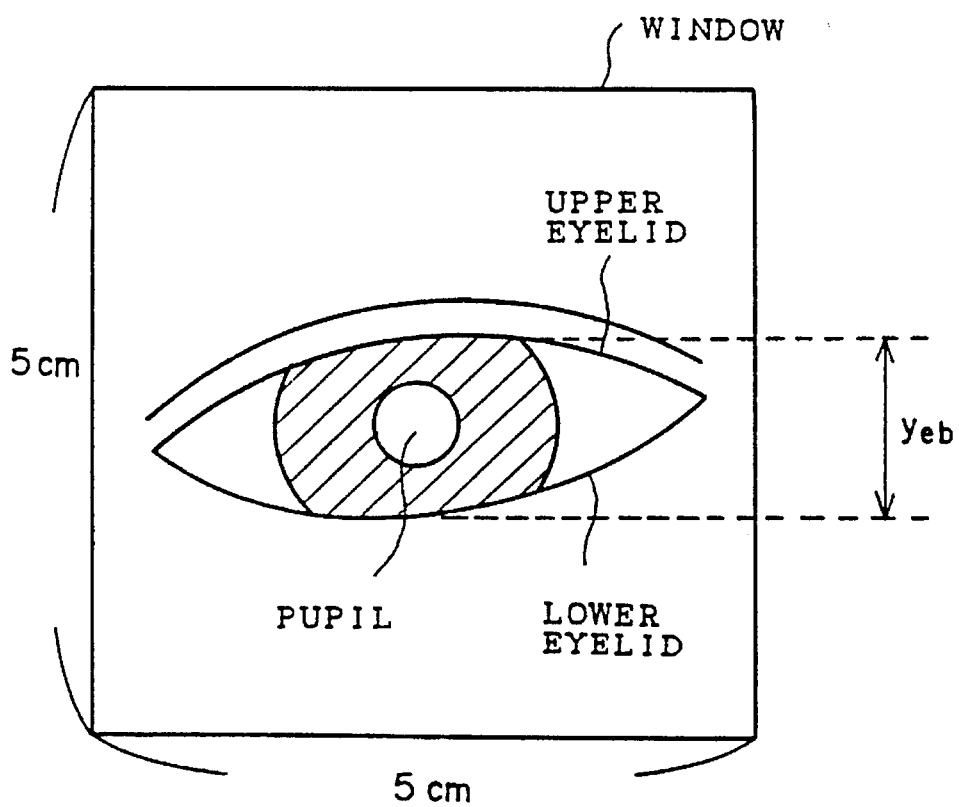
FIG. 27 is a view depicting how the ninth embodiment works illustratively.
Figure 28:
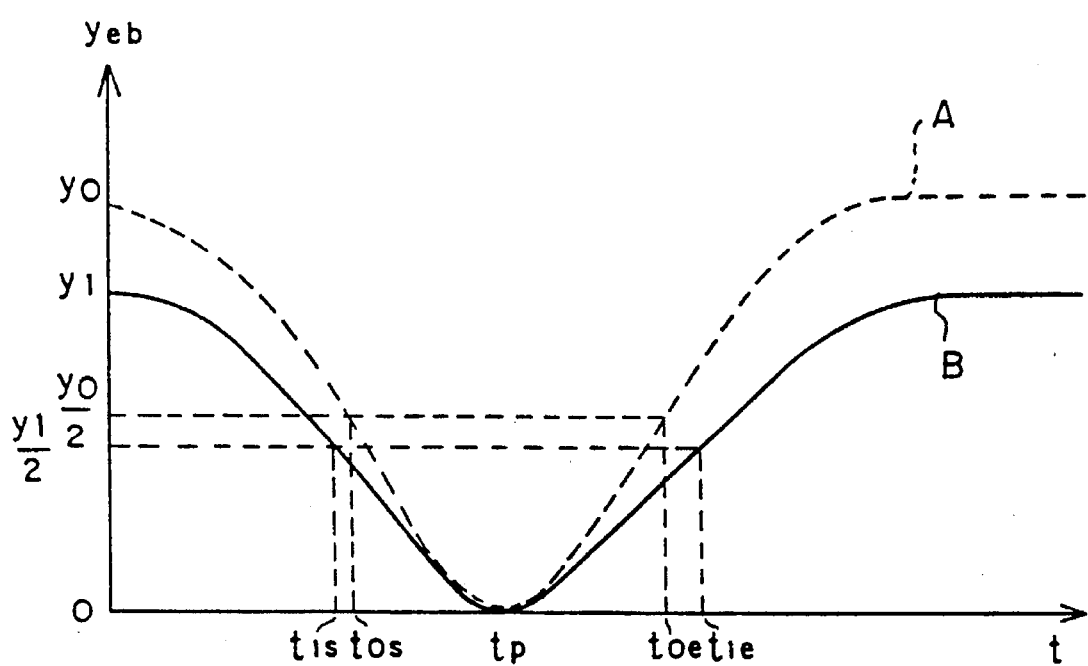
FIG. 28 is another graphic representation indicating how the ninth embodiment works illustratively.

Whereas the eighth embodiment is a variation of the sixth embodiment supplemented with the zoom mechanism, any one of the first through the fifth embodiments and of the seventh embodiment may be provided with the zoom mechanism as well. Such an arrangement makes it possible to find the exact shape of the pupil, whereby the accuracy of bodily state detection is improved.
Ninth Embodiment FIG. 25 is a schematic view of a bodily state detection apparatus in a preferred structure according to the ninth embodiment of the invention. Whereas the fourth embodiment has estimated the degree of eyelid opening on the basis of the pupil shape obtained, the ninth embodiment extracts first the pupils and then the eyelids. The degree of eyelid opening is calculated directly from the eyelids so extracted. The waveform representing the subject person' blinks is then acquired from the degrees of eyelid opening, whereby the degrees of alertness are detected. In general, the blinking frequency occurs as shown in FIG. 26. In this figure, the axis of ordinate $Y_{eb}$ represents the maximum vertical distance of the upper and lower eyelids (see FIG. 27), and $Y_0$ denotes the maximum distance between the upper and lower eyelids when they are most wide apart. The axis of abscissa t stands for time, $t_p$ denotes the time at which the eyelids are fully closed, and $t_{0s}$ and $t_{0e}$ each represent the time of $y_0/2$. FIG. 28 shows two blinking waveforms, one appearing when the degree of alertness drops (along solid curved line B), the other occurring when the degree of alertness has not dropped (along broken curved line A). Apart from slight personal differences, drops in alertness are generally accompanied by the slowing of the blinking waveform. Along the solid curved line B in FIG. 28, $y_1$ represents the maximum distance between the fully opened eyelids, and $t_{1s}$ and tie each denote the time of $y_1/2$.

The ninth embodiment works as follows: referring to FIG. 25, the window setting circuit 22 determines the range (window) of search for the eyelids with respect to the eyelid position extracted by the pupil extraction circuit 21. As shown in FIG. 27, a window 5 cm square is set around the pupil in search of the upper and lower eyelids. From inside the window set by the window setting circuit 22, the feature point extraction circuit 23 extracts the eyelids according to the rate of brightness changes in the vertical direction of the image, and obtains the maximum distance $y_{eb}$ between the upper and lower eyelids. The extraction result memory 30 stores the changes over time in the maximum distance $y_{eb}$ as a blinking waveform. The drowsiness judgment circuit 40 recognizes the pattern of this blinking waveform, analyzes it, and judges the subject person to be drowsy if the frequency of occurrences of the alertness-reduced waveform becomes higher than a predetermined value. The analysis of blinking waveforms relies generally on blinking duration $(t_e-t_s)$ or on the ratio of eyelid closing speed to eyelid opening speed $(t_p-t_s)/(t_e-t_p)$ ($t_{1s}$ and $t_{0s}$ are represented generically by $t_s$, and $t_{1e}$ and $t_{0e}$ by $t_e$). The ninth embodiment utilizes the blinking duration $t_e-t_s$; when the duration exceeds a predetermined value, the subject person is judged to be drowsy.

Although the ninth embodiment has acquired $t_e$ and $t_s$ from y/2, this is not limitative of the invention. Alternatively, the values at y/3 may be used instead.

Whereas the ninth embodiment analyzes blinking waveforms for detection of drowsiness, the blinking frequency may alternatively be obtained from the degree of eyelid opening, and the degree of alertness may be acquired on the basis of the blinking frequency so obtained. As with the fourth embodiment, the half-closed state of the eyelids may be judged from the degree of eyelid opening, and the degree of alertness may be detected as per the half-closed state of the eyelids.

Although the ninth embodiment extracts the eyelids from the window set up specifically to extract the eyelids with respect to the pupil position, this is not limitative of the invention. Alternatively, there may be established a window from which to extract the iris with respect to the pupil position. In this setup, the iris is extracted through edge detection and Hough transformation. As with the fourth embodiment, the degree of eyelid opening is then estimated in accordance with the iris size, and the subject person's degree of alertness is detected from the degree of eyelid opening so estimated.

Tenth Embodiment

Figure 29:
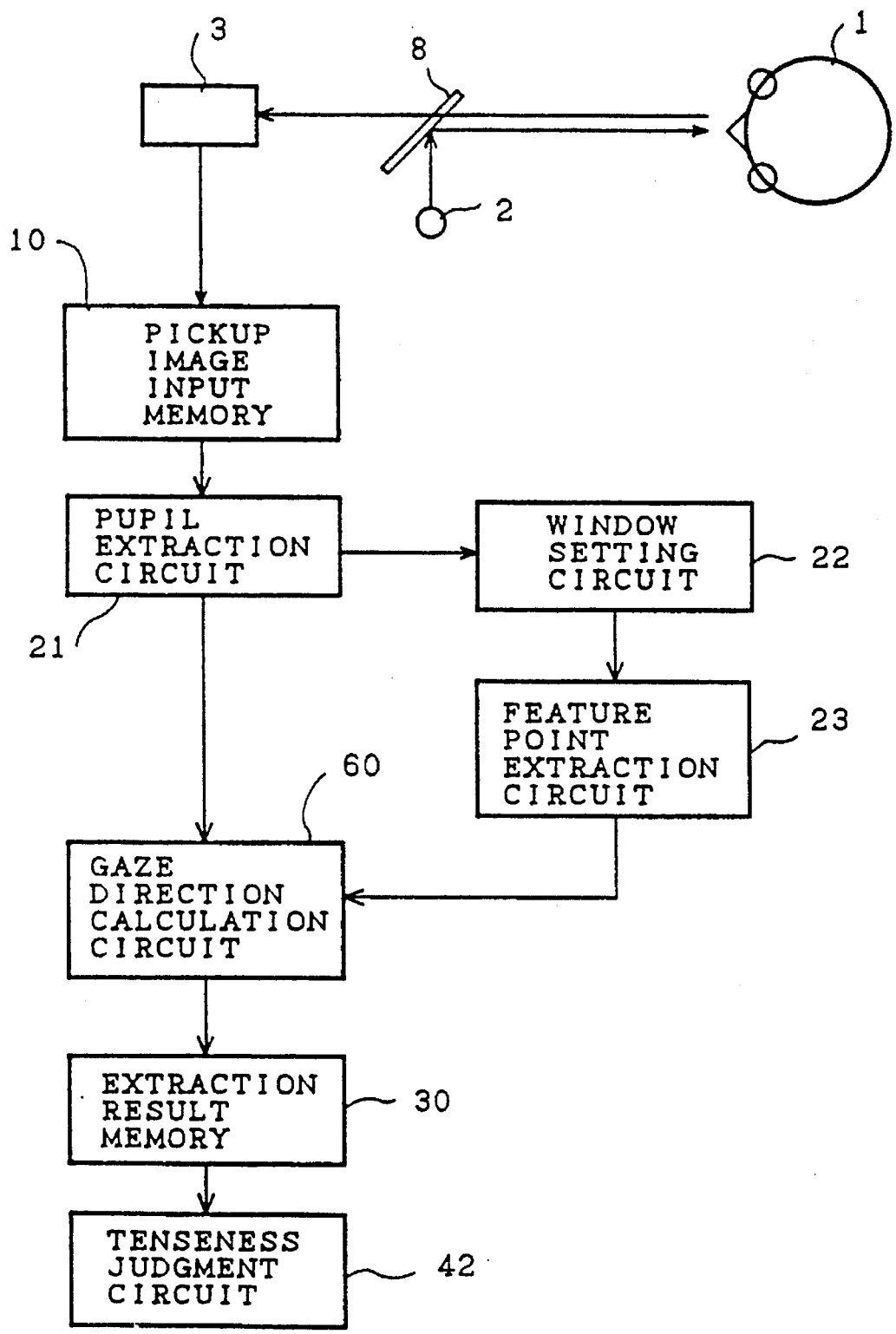
FIG. 29 is a schematic view of a bodily state detection apparatus practiced as a tenth embodiment of the invention.

FIG. 29 is a schematic view of a bodily state detection apparatus in a preferred structure according to the tenth embodiment of the invention. Whereas the seventh embodiment has measured the average diameter of the pupils to detect the subject person's degree of tenseness, the tenth embodiment first extracts the pupils, then finds the gaze direction, and detects the subject person's degree of tenseness based on the time series patterns of the gaze direction. In FIG. 29, reference numeral 60 is a gaze direction calculation circuit.

Figure 30A:
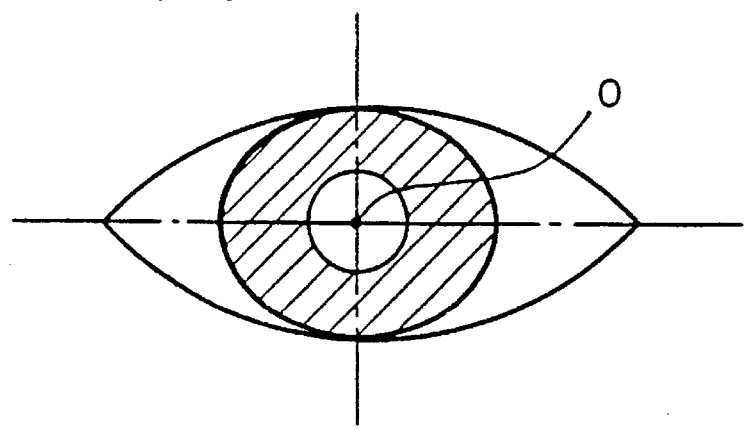
FIGS. 30(a), 30(b) and 30(c) are views demonstrating how the tenth embodiment works illustratively.
Figure 30B:
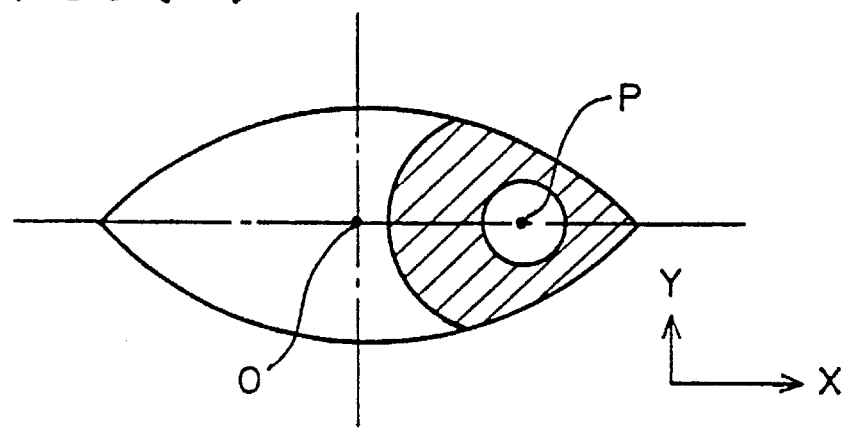
Figure 30C:
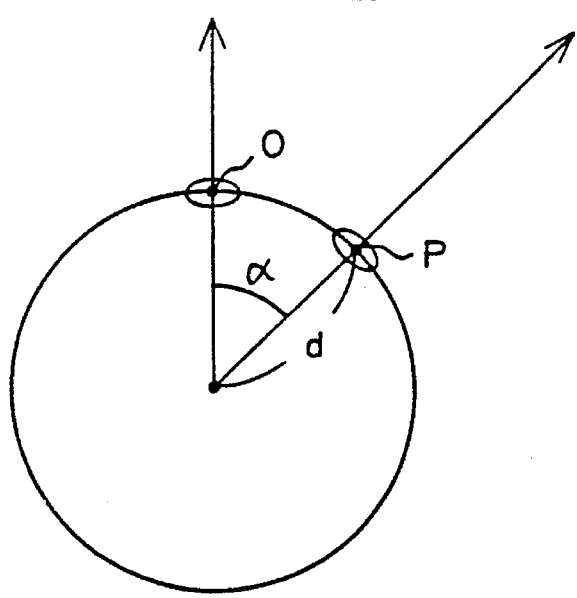

The tenth embodiment works as follows: referring to FIG. 29, the window setting circuit 22 sets up the range (window) of search for the eyelids with respect to the pupil position extracted by the pupil extraction circuit 21, as in the case of the ninth embodiment. The feature point extraction circuit 23 extracts the eyelids from inside the window set up by the window setting circuit 22. The gaze direction calculation circuit 60 estimates the gaze direction based on the positional relationship between the eyelids and the pupils. FIGS. 30(a) through 30(c) show how the gaze directions are determined illustratively. FIG. 30(a) is a view of an eye gazing on the front (i.e., toward the camera), FIG. 30(b) is a view of an eye gazing on the right, and FIG. 30(c) depicts the gaze direction as viewed from above. When the midpoint O between the upper and lower lids (i.e., the position corresponding to the center of the pupil as the subject person faces the front) and the apparent pupil center P are known, the gaze direction is obtained as per the positional relationship between O and P. That is, X-axis distance of OP=d-sin($\alpha$)

Y-axis distance of OP=d-sin($\beta$)

where, d: radius of eyeball (1.22 cm, the Japanese average, for the tenth embodiment)

$\alpha$: angle of gaze in X-axis direction $\beta$: angle of gaze in Y-axis direction The extraction result memory 30 stores time series patterns of the gaze directions $\alpha$ and $\beta$ acquired by the gaze direction calculation circuit 60 (FIG. 31(a) shows a typical time series pattern of the gaze direction $\alpha$). When the subject person becomes languid, the movement of gaze directions decreases in dispersion (as shown in FIG. 31(b-1)). Thus the tenseness judgment circuit 42 acquires the dispersion of the gaze direction movement (FIG. 31(b-1)) plots the dispersion of the gaze direction movement in FIG. 31(a)) using the equation:

$$\text{dispersion} = 1/2 \overset{N}{\Sigma} |\text{average} - \text{individual value}|$$

When the dispersion in the movement of the gaze direction $\alpha$ becomes lower than a predetermined level within a predetermined period of time (e.g., 2 minutes), the tenseness judgment circuit 42 judges the subject person to be in a languid state.

Eleventh Embodiment

Figure 32:
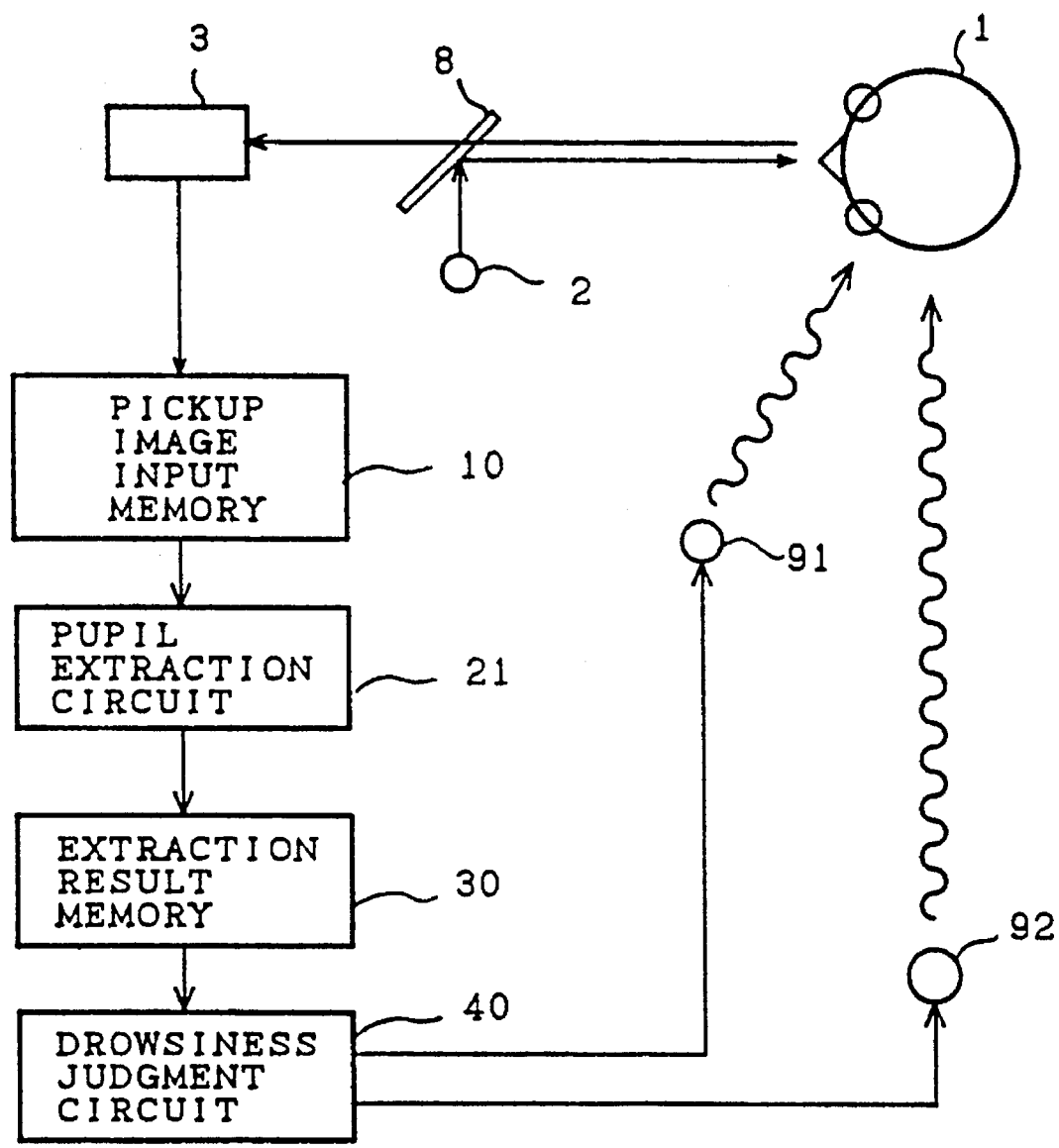
FIG. 32 is a schematic view of a bodily state detection apparatus practiced as an eleventh embodiment of the invention.

FIG. 32 is a schematic view of a bodily state detection apparatus in a preferred structure according to the eleventh embodiment of the invention. Some of the preceding embodiments have detected the subject person's bodily state, and some have activated the buzzer upon detecting that state. By contrast, the eleventh embodiment keeps detecting the subject person's bodily state even after the buzzer has been activated in order to increase the accuracy of bodily state detection. In FIG. 32, reference numeral 91 is a visible LED device (stimulus generation means) and 92 is a buzzer.

The eleventh embodiment works as follows: referring to FIG. 32, the pupil extraction circuit 21 and extraction result memory 30 operate in the same manner as those of the second embodiment; time series data about the pupil positions are accommodated in the memory 30. The drowsiness judgment circuit 40 judges the subject person's drowsiness according to the duration of that person's "downcast" state derived from the time series data on the pupil positions held in the extraction result memory 30. If the subject person 1 is judged provisionally to be drowsy, the visible LED device 91 is activated to illuminate that person. The subject person's state before activation of the visible LED device 91 is compared with that person's state thereafter. If the subject person's state after activation of the visible LED device 91 remains the same as before, the drowsiness judgment circuit 40 judges that person to be indeed drowsy and activates the buzzer 92.

Figure 33:
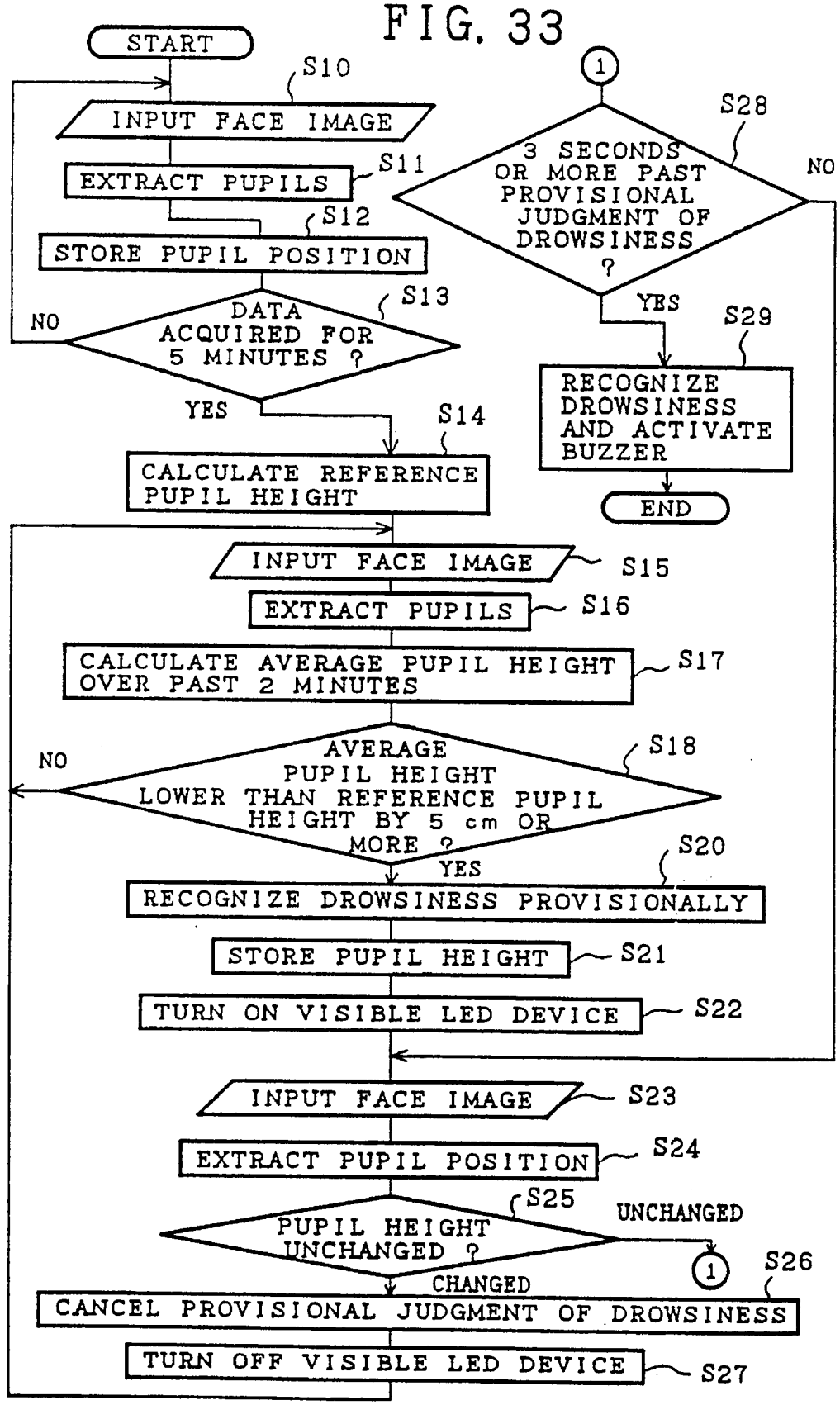
FIG. 33 is a flowchart of steps in which the eleventh embodiment operates.

The detailed workings of the eleventh embodiment are depicted in the flowchart of FIG. 33. In FIG. 33, steps 10 through 18 are the same as those in FIG. 10 for the second embodiment. In step 20, the subject person is judged provisionally to be drowsy (primary result of judgment). In step 21, the pupil position in effect at this point is stored. In step 22, the visible LED device 91 is turned on. In step 23, another face image is input. In step 24, the pupil position is extracted in the same manner as in step 11. In step 25, a check is made to see if the pupil position (i.e., pupil height) extracted in step 24 differs from the pupil position stored in step 21. If the two positions are different, step 26 is reached in which the provisional judgment of drowsiness is canceled. In step 27, the visible LED 91 is turned off. If the pupil position remains unchanged, step 28 is reached. In step 28, the subject person is judged provisionally to be drowsy and a check is made to see if three seconds have elapsed. If three seconds have yet to elapse in step 28, step 23 is reached again in which another face image is picked up. If three second have elapsed in step 28, the "downcast" state is judged to remain unchanged after the alarm. Thus the subject person is judged to be indeed drowsy (secondary result of judgment), and the buzzer 92 is activated.

The eleventh embodiment is in fact a variation of the second embodiment supplemented with the ability to compare the subject person's state before application of stimulus and the state thereafter. Alternatively, any one of the other preceding embodiments may be arranged to give stimulus to the subject person depending on that person's state. Comparing the subject person's states before and after application of the stimulus gives an indication of that person's current bodily state.

For the eleventh embodiment, the visible LED device 91 may be replaced with a soft-sounding buzzer or any other device that will stimulate any one of the subject person's five senses. Where the embodiment is used illustratively for an operator at the console of a plant, a voice message such as "Push this button, please" may be given as the stimulus.

Twelfth Embodiment

Figure 34:
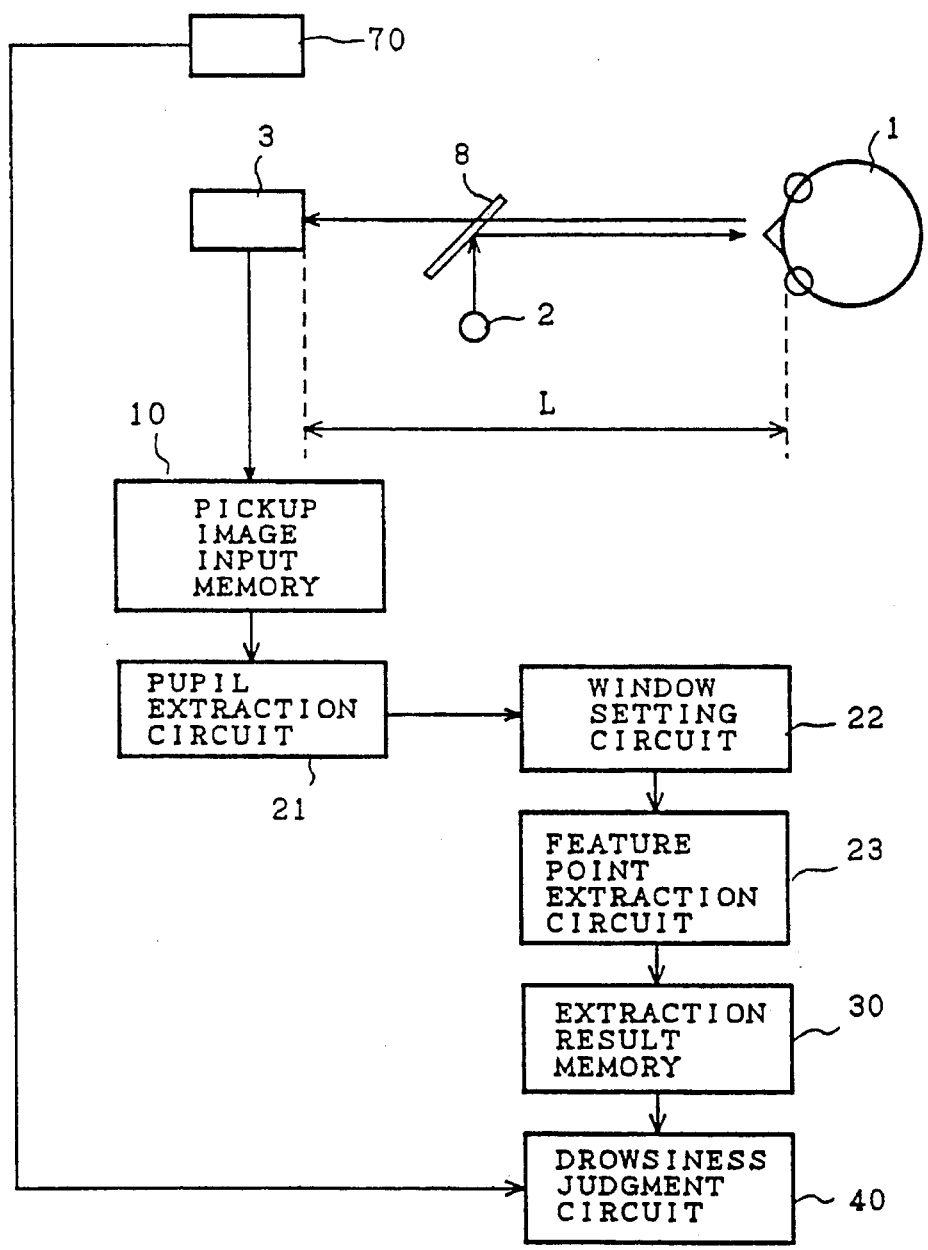
FIG. 34 is a schematic view of a bodily state detection apparatus practiced as a twelfth embodiment of the invention.
Figure 35A:
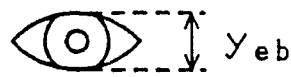
FIGS. 35(a) and 35(b) are a view explaining how the twelfth embodiment works illustratively.
Figure 35B:
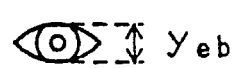

FIG. 34 is a schematic view of a bodily state detection apparatus in a preferred structure according to the twelfth embodiment of the invention. The preceding embodiments have detected the position and/or the shape of the subject person's feature points such as the eyelids on the assumption that the distance to that person stays constant. However, in cases like the one in FIG. 35(b) in which the distance L between the camera and the subject person is prolonged, the pupils and eyelids appear appreciably small in apparent size.

If $L_0$ denotes the reference distance between the subject person 1 and the camera 3, then the apparent size of, say, eyelids $y_{eb}$ is represented by $Y_{eb} \cdot L_0/L$, where $Y_{eb}$ stands for the eyelid size seen over the reference distance.

The twelfth embodiment has the ability to correct changes in the apparent pupil shape or feature quantities when distances between the subject person 1 and the camera 3 change. This embodiment is in fact a variation of the ninth embodiment supplemented with the correction means. In FIG. 34, reference numeral 70 is an ultrasonic sensor-based distance measurement circuit located close to the CCD camera 3.

The twelfth embodiment works as follows: the ultrasonic sensor-based distance measurement circuit 70 emits ultrasonic pulses to the subject person 1. The circuit 70 finds the distance L by calculating the time required for the ultrasonic wave to hit the subject person 1, to be reflected thereby and to return to its origin. The equation utilized for the calculation of the distance L is:

$$L = v \cdot t/2$$

where, v is the velocity of ultrasonic wave propagation, and t is the time required for the emitted wave to return to its origin. When the distance L between the subject person 1 and the camera 3 is measured, the distance $y_{eb}$ acquired by the ninth embodiment is corrected as per the measured distance L using the equation:

$$Y_{eb} = y_{eb} \cdot L/L_0$$

This provides the blinking waveform. The rest of the steps for drowsiness detection are the same as those of the ninth embodiment.

Whereas the twelfth embodiment is a variation of the ninth embodiment supplemented with the distance correction means, any one of the other preceding embodiments may be equipped with a similar capability. That is, the distance between a predetermined position and the subject person's face may be measured. Then the pupil shape or the feature quantities may be corrected according to the measured distance, whereby the accuracy of drowsiness detection is boosted.

Although the twelfth embodiment has employed the ultrasonic sensor as the distance measurement means, this is not limitative of the invention. Alternatively, the distance to the subject person may be measured from the focal point of the camera lens. Another alternative is to have the subject person wear a position measuring magnetic sensor on the head. A further alternative is to provide a plurality of coaxial illumination devices that acquire the distance to a feature point on the subject person's face through triangulation.

Thirteenth Embodiment

Figure 36:
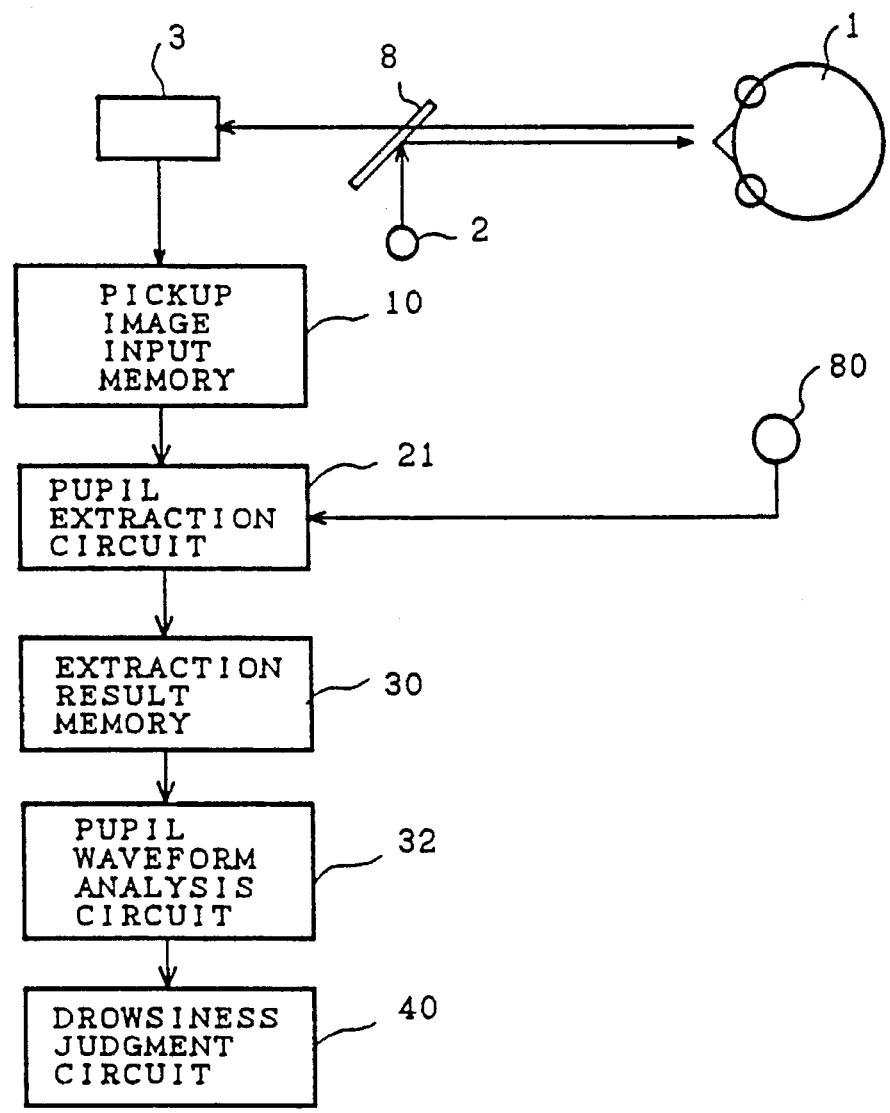
FIG. 36 is a schematic view of a bodily state detection apparatus practiced as a thirteenth embodiment of the invention.
Figure 37:
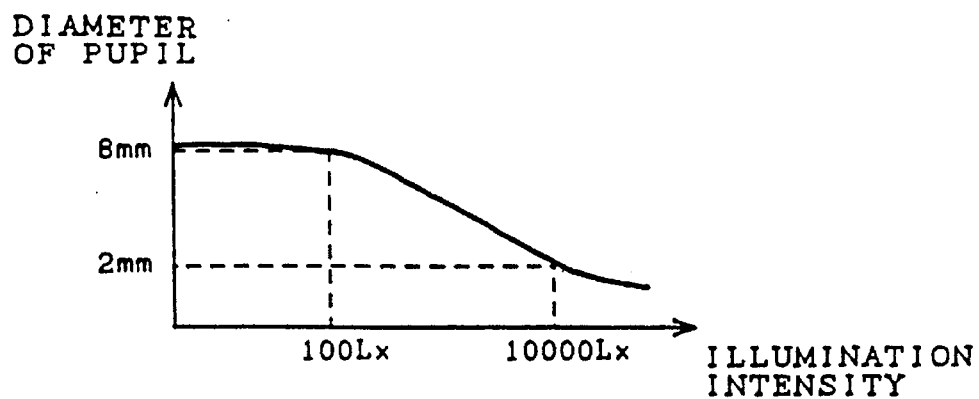
FIG. 37 is a graphic representation demonstrating how the thirteenth embodiment works illustratively.

FIG. 36 is a schematic view of a bodily state detection apparatus in a preferred structure according to the thirteenth embodiment of the invention. The preceding embodiments have detected the pupil shape on the assumption that the intensity of illumination around the subject person is constant. However, as shown in FIG. 37, the pupils become smaller the higher the intensity of illumination. It follows that errors can occur in detecting the pupil shape when the illumination intensity varies. This difficulty is bypassed by the thirteenth embodiment having the ability to correct changes in the detected pupil shape when the intensity of illumination varies around the subject person. This embodiment is in fact a variation of the sixth embodiment supplemented with the correction means. In FIG. 36, reference numeral 80 is an illumination sensor located near the subject person.

The thirteenth embodiment works as follows: the illumination sensor 80 measures the intensity of illumination around the subject person. Given the sensor output, the pupil extraction circuit 21 corrects the extracted pupil diameter by multiplying it by a coefficient commensurate with the previously acquired illumination intensity. This arrangement makes it possible to analyze the waveform of pupil fluctuations regardless of the varying illumination intensity.

Alternatively, the moment the illumination intensity has changed, the result of the analysis regarding the current pupil waveform may be discarded and a new pupil waveform may be taken up for renewed analysis.

Fourteenth Embodiment

Figure 38:
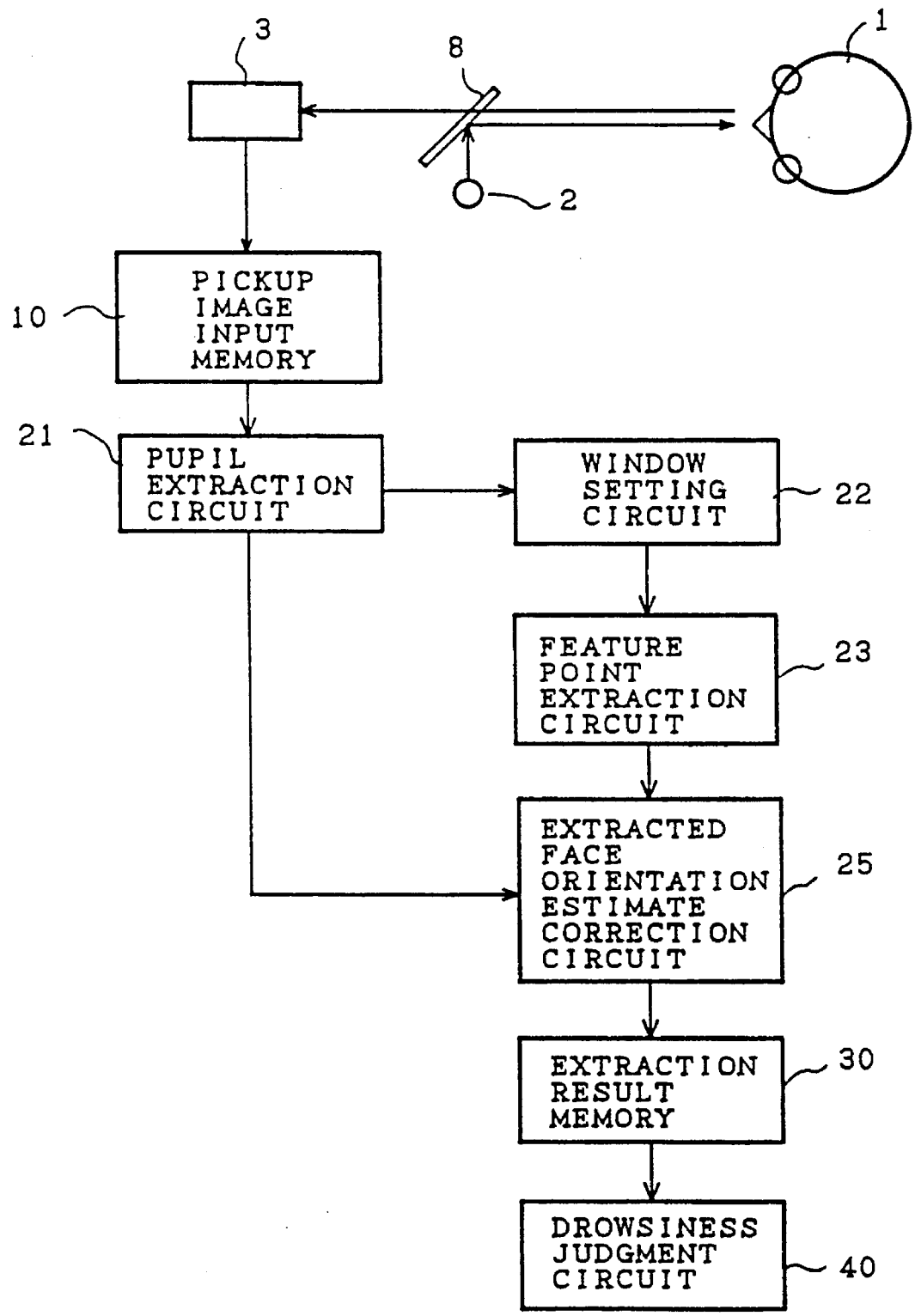
FIG. 38 is a schematic view of a bodily state detection apparatus practiced as a fourteenth embodiment of the invention.

FIG. 38 is a schematic view of a bodily state detection apparatus in a preferred structure according to the fourteenth embodiment of the invention. The ninth embodiment has judged the subject person's alertness in accordance with the distance between that person's upper and lower eyelids. That setup works well as long as the subject person does not tilt his face vertically. If the face does tilt, the apparent distance between the upper and lower eyelids becomes shorter. The fourteenth embodiment has the ability to correct the changes in the pupil shape or feature quantities stemming from the subject person's tilting his face vertically. This embodiment is in fact a variation of the ninth embodiment supplemented with the correction means. In FIG. 38, reference numeral 25 is an extracted face orientation estimate correction circuit.

The fourteenth embodiment works as follows: the vertical angle of the subject person's face is obtained in the same manner as with the third embodiment. That is, the pupil position acquired by the pupil extraction circuit 21 and the nostril position obtained by the feature point extraction circuit 23 are input to the extracted face orientation estimate correction circuit 25. The circuit 25 first finds two distances: distance S0 between the pupil center and the nostril center in effect when the subject person faces the front, and apparent distance S between the pupil center and the nostril center. Using the distances S0 and S, the circuit 25 obtains the vertical angle θ. The equation utilized is:

$$S = S0 \cdot \cos(\theta)$$

Meanwhile, the feature point extraction circuit 23 extracts the eyelids in the same manner as that of the ninth embodiment. When the maximum distance $y_{eb}$ between the upper and lower eyelids is obtained, that distance is input to the extracted face orientation estimate correction circuit 25. In turn, the circuit 25 corrects the distance between the upper and lower eyelids based on the angle θ and distance $y_{eb}$ acquired above. The equation employed is:

$$y_h = y_{eb} / \cos(\theta)$$

where, $y_{eb}$ is the distance between the upper and lower eyelids extracted from the face image, $y_h$ is the corrected distance between the upper and lower eyelids, and θ is the vertical rotation angle of the subject person's face (the angle is 0 when that person faces the front). The extraction result memory 30 stores the changes over time in the corrected distance $y_h$ as a blinking waveform. The drowsiness judgment circuit 40 recognizes the pattern of that blinking waveform, analyzes it, and judges the subject person to be drowsy if the frequency of occurrences of the alertness-reduced waveform becomes higher than a predetermined value.

Whereas the fourteenth embodiment is a variation of the ninth embodiment supplemented with the ability to make corrections according to the vertical face angle, any one of the other embodiments may be equipped with a similar capability. That is, the vertical or horizontal angle of the subject person's face may be measured, and the pupil shape or feature quantities may be corrected in keeping with the angle so measured, whereby the accuracy of drowsiness detection is improved.

To sum up and according to the first aspect of the invention, the bodily state detection apparatus comprises: optical input means for receiving images of a predetermined area including the face of a subject person; illumination means for illuminating the subject person in such a manner that the direction of the illumination coincides substantially with the optical axis connecting the subject person with the optical input means; pupil extraction means for extracting either the pupil position or the pupil shape of the subject person from the images thereof output from the optical input means; and bodily state judgment means for judging the bodily state of the subject person by use of the result of the pupil extraction performed by the pupil extraction means. Constituted in this manner, the apparatus extracts the subject person's pupils through simplified image processing for easy, noncontact judgment of that person's bodily state.

According to the second aspect of the invention, the bodily state detection apparatus comprises: optical input means for receiving images of a predetermined area including the face of a subject person; illumination means for illuminating the subject person in such a manner that the direction of the illumination coincides substantially with the optical axis connecting the subject person with the optical input means; pupil extraction means for extracting either the pupil position or the pupil shape of the subject person from the images thereof output from the optical input means; search range definition means for defining the range of search for feature points in the subject person's face on the basis of the result of the pupil extraction performed by the pupil extraction means; feature quantity extraction means for extracting either the position or the shape of the feature points in the range defined by the search range definition means; and bodily state judgment means for judging the bodily state of the subject person by use of the result of the feature quantity extraction performed by the feature quantity extraction means or by use of the result of pupil extraction performed by the pupil extraction means. Constituted in this manner, the apparatus enhances the accuracy of bodily state detection by acquiring the relevant feature quantities more directly than before.

In a preferred structure according to the third aspect of the invention, the bodily state detection apparatus further comprises extraction result storage means for storing the result of the pupil extraction or feature quantity extraction, wherein the bodily state judgment means judges the bodily state of the subject person in accordance with the stored contents of the extraction result storage means. This structure allows the apparatus to utilize time series averaged data, thereby enhancing the accuracy of bodily state detection.

In a preferred structure according to the fourth aspect of the invention, the bodily state detection apparatus further comprises eyelid opening estimation means for estimating the degree of eyelid opening of the subject person in accordance with the pupil shape extracted by the pupil extraction means, wherein the bodily state judgment means judges the bodily state of the subject person on the basis of the estimated degree of eyelid opening. From the bodily state so judged, the apparatus recognizes the subject person's blinking state and the degree of his alertness accordingly.

In a preferred structure according to the fifth aspect of the invention, the bodily state detection apparatus further comprises blinking frequency estimation means for estimating the frequency of blinking of the subject person in accordance with the result of the pupil extraction, wherein the bodily state judgment means judges the bodily state of the subject person on the basis of the estimated frequency of blinking. With the subject person's blinking frequency estimated as in the preceding structure, it is possible for the apparatus to recognize the degree of alertness or tenseness of that person.

In a preferred structure according to the sixth aspect of the invention, the bodily state detection apparatus further comprises pupil waveform output means for measuring the diameter of the pupils from the pupil shape extracted by the pupil extraction means and for outputting waveforms of expansion and contraction of the pupils of the subject person, wherein the bodily state judgment means judges the subject person's bodily state in accordance with the waveforms of expansion and contraction of that person's pupils. After determining how the subject person's pupils expand and contract, the apparatus judges the physiological state or the degree of tenseness of that person.

In a preferred structure according to the seventh aspect of the invention, the pupil waveform output means measures the maximum diameter of the pupils from the pupil shape extracted by the pupil extraction means, whereby the waveforms of expansion and contraction of the subject person's pupils are output. This structure makes it possible to estimate correctly the pupil size regardless of the changing face orientation. The apparatus thus provides higher reliability than before.

In a preferred structure according to the eighth aspect of the invention, the bodily state detection apparatus further comprises eyelid opening calculation means for calculating the degree of eyelid opening of the subject person in accordance with the result of eyelid feature quantity extraction performed by the feature quantity extraction means, wherein the bodily state judgment means judges the bodily state of the subject person on the basis of the calculated degree of eyelid opening. Because the subject person's blinking state is known unfailingly in the above manner, it is possible for the apparatus to judge that person's degree of alertness more reliably than before.

In a preferred structure according to the ninth aspect of the invention, the bodily state detection apparatus further comprises gaze direction detection means for detecting the gaze direction of the subject person in accordance with the result of pupil extraction by the pupil extraction means and with the result of feature quantity extraction by the feature quantity extraction means, wherein the bodily state judgment means judges the bodily state of the subject person on the basis of time series patterns of the subject person's gaze direction. This structure allows the apparatus to find the degree of tenseness of the subject person.

In a preferred structure according to the tenth aspect of the invention, the bodily state detection apparatus further comprises stimulus generation means for generating stimulus to the subject person depending on the primary result of judgment by the bodily state judgment means, wherein the bodily state judgment means makes a secondary judgment on the bodily state of the subject person in accordance with the status of either the pupils or the feature points before and after the generation of the stimulus. Using the first and secondary judgments, this structure allows the apparatus to afford higher accuracy than before in bodily state detection.

In a preferred structure according to the eleventh aspect of the invention, the bodily state detection apparatus further comprises face distance measurement means for measuring the distance between a predetermined position and the face of the subject person, wherein the pupil extraction means or the feature quantity extraction means corrects the extracted pupil shape or feature quantities in accordance with the measured distance. With the face distance so measured, the apparatus corrects the pupil shape or the feature quantities correspondingly, thus enhancing the accuracy of bodily state detection.

In a preferred structure according to the twelfth aspect of the invention, the bodily state detection apparatus further comprises illumination measurement means for measuring the intensity of illumination near the subject person, wherein the bodily state judgment means judges the bodily state of the subject person in accordance with the result of the measured intensity of illumination. Based on the illumination intensity so measured, the apparatus judges the subject person's bodily state with higher accuracy than before.

In a preferred structure according to the thirteenth aspect of the invention, the bodily state detection apparatus further comprises face orientation estimation means for measuring the face orientation of the subject person, wherein the pupil extraction means or feature quantity extraction means corrects the pupil shape or feature quantities in accordance with the measured face orientation. With the face orientation so determined, the apparatus corrects the pupil shape or feature quantities correspondingly, whereby the accuracy of bodily state detection is boosted.

In a preferred structure according to the fourteenth aspect of the invention, the bodily state detection apparatus further comprises magnification means for magnifying the images of the predetermined area including the face of the subject person, the magnified images being input to the optical input means. When the magnified images are input to the optical input means, the apparatus detects the subject person's bodily state with higher accuracy than before.

While preferred embodiments of the invention have been described using specific terms, such description is for illustrative purposes only, and it is to be understood that changes and variations may be made without departing from the spirit or scope of the following claims.

What is claimed is:

1. A bodily state detection apparatus comprising:

optical input means for receiving images of a predetermined area including the face of a subject person;

illumination means for illuminating said subject person, said illumination means being positioned so that at least near said subject person, the direction of illumination substantially coincides with an optical axis from said subject person to said optical input means;

pupil extraction means for extracting at least one of pupil position and pupil shape of said subject person based upon brightest locations of the images output from said optical input means; and bodily state judgment means for judging the bodily state of said subject person by use of the result of the pupil extraction performed by said pupil extraction means.

2. A bodily state detection apparatus according to claim 1, further comprising extraction result storage means for storing the result of said pupil extraction, wherein said bodily state judgment means judges the bodily state of said subject person by use of the stored contents of said extraction result storage means.

3. A bodily state detection apparatus according to claim 1, further comprising eyelid opening estimation means for estimating the degree of eyelid opening of said subject person in accordance with the pupil shape extracted by said pupil extraction means, wherein said bodily state judgment means judges the bodily state of said subject person by use of the estimated degree of eyelid opening.

4. A bodily state detection apparatus according to claim 1, further comprising blinking frequency estimation means for estimating the frequency of blinking of said subject person in accordance with the result of said pupil extraction, wherein said bodily state judgment means judges the bodily state of said subject person on the basis of said frequency of blinking.

5. A bodily state detection apparatus according to claim 1, further comprising pupil waveform output means for measuring the diameter of the pupils from the pupil shape extracted by said pupil extraction means and for outputting waveforms of expansion and contraction of the pupils of said subject person, wherein said bodily state judgment means judges the bodily state of said subject person in accordance with said waveforms of expansion and extraction of the pupils.

6. A bodily state detection apparatus according to claim 5, wherein said pupil waveform output means measures the maximum diameter of the pupils from the pupil shape extracted by said pupil extraction means, thereby outputting the waveforms of expansion and contraction of the pupils of said subject person.

7. A bodily state detection apparatus according to claim 1, further comprising stimulus generation means for generating stimulus to said subject person depending on the primary result of judgment by said bodily state judgment means, wherein said bodily state judgment means makes a secondary judgment on the bodily state of said subject person in accordance with the status of the pupils before and after the generation of said stimulus.

8. A bodily state detection apparatus according to claim 1, further comprising face distance measurement means for measuring the distance between a predetermined position and the face of said subject person, wherein said pupil extraction means corrects the pupil shape in accordance with the measured distance.

9. A bodily state detection apparatus according to claim 1, further comprising illumination measurement means for measuring the intensity of illumination near said subject person, wherein said bodily state judgment means judges the bodily state of said subject person in accordance with the result of the measured intensity of illumination.

10. A bodily state detection apparatus according to claim 1, further comprising face orientation estimation means for measuring the face orientation of said subject person, wherein said pupil extraction means corrects the pupil shape in accordance with the measured face orientation.

11. A bodily state detection apparatus according to claim 1, further comprising magnification means for magnifying the images of said predetermined area including the face of said subject person, the magnified images being input to said optical input means.

12. The bodily state detection apparatus of claim 1, wherein said illumination means includes:

a light generator positioned away from the optical axis from said subject person to said optical input means; and a light reflector which reflects light from the light generator toward said subject person along the optical axis from said subject person and said optical input means.

13. The bodily state detection apparatus of claim 12, wherein said light reflector is positioned along the optical axis from said subject person to said optical input means, and allows light reflected from said subject person to pass to said optical input means.

14. The bodily state detection apparatus of claim 13, wherein said light reflector is a half mirror.

15. The bodily state detection apparatus of claim 12, wherein said light generator is an infrared LED.

\* \* \* \* \*